(12) United States Patent
Lazarev et al.

(10) Patent No.: US 12,237,083 B2
(45) Date of Patent: Feb. 25, 2025

(54) DIFFRACTION-BASED GLOBAL IN VITRO DIAGNOSTIC SYSTEM

(71) Applicant: Bragg Analytics, Inc., Menlo Park, CA (US)

(72) Inventors: Pavel Lazarev, Menlo Park, CA (US); Alexander Lazarev, Lake Forest, CA (US)

(73) Assignee: Bragg Analytics, Inc., Menlo Park, CA (US)

( * ) Notice: Subject to any disclaimer, the term of this patent is extended or adjusted under 35 U.S.C. 154(b) by 26 days.

(21) Appl. No.: 17/593,845

(22) PCT Filed: Jun. 14, 2021

(86) PCT No.: PCT/US2021/037238
§ 371 (c)(1),
(2) Date: Sep. 26, 2021

(87) PCT Pub. No.: WO2021/257457
PCT Pub. Date: Dec. 23, 2021

(65) Prior Publication Data
US 2023/0207074 A1      Jun. 29, 2023

Related U.S. Application Data

(60) Provisional application No. 63/039,340, filed on Jun. 15, 2020.

(51) Int. Cl.
*G16H 50/20* (2018.01)
*A61B 5/00* (2006.01)
(Continued)

(52) U.S. Cl.
CPC .............. *G16H 50/20* (2018.01); *A61B 5/00* (2013.01); *A61B 5/4312* (2013.01); *G01N 23/20* (2013.01);
(Continued)

(58) Field of Classification Search
CPC ........ G16H 50/20; G16H 10/40; G16H 10/60; G16H 30/20; G16H 40/63; G16H 40/67;
(Continued)

(56) References Cited

U.S. PATENT DOCUMENTS

| 5,717,733 A | 2/1998 | Kurbatov et al. |
| 6,175,117 B1 | 1/2001 | Komardin et al. |

(Continued)

FOREIGN PATENT DOCUMENTS

| EP | 3547181 A1 | 10/2019 | |
| JP | 2003070804 A | * 3/2003 | ........... A61B 1/0004 |

(Continued)

OTHER PUBLICATIONS

James, "A Review of Low Angle Fibre Diffraction in the Diagnosis of Disease", British Journal of Medicine & Medical Research, 3(2): 383-397, Feb. 19, 2013.

(Continued)

*Primary Examiner* — Kiho Kim
(74) *Attorney, Agent, or Firm* — WILSON SONSINI GOODRICH & ROSATI

(57) ABSTRACT

Provided herein are diffractometer-based global diagnostic systems and uses thereof. The systems may comprise one or more diffraction apparatus operatively coupled to a computer database over a network. The one or more diffraction apparatus may be configured for transfer of data such as pathology lab image data, diffraction pattern data, subject data, or any combination thereof to the computer database over the network. The systems may further comprise one or more computer processors operatively coupled to the one or more diffraction apparatus, which computer processors may be configured to receive the data from the diffraction apparatus, transmit the data to the computer database, and process the data using a data analytics algorithm which may (Continued)

provide a computer-aided diagnostic indicator for the individual subject.

20 Claims, 10 Drawing Sheets

(51) Int. Cl.

| | |
|---|---|
| G01N 23/20 | (2018.01) |
| G01N 23/201 | (2018.01) |
| G01N 33/483 | (2006.01) |
| G06F 21/60 | (2013.01) |
| G06N 3/08 | (2023.01) |
| G06Q 20/08 | (2012.01) |
| G06Q 20/32 | (2012.01) |
| G16H 10/40 | (2018.01) |
| G16H 10/60 | (2018.01) |
| G16H 30/20 | (2018.01) |
| G16H 40/63 | (2018.01) |
| G16H 40/67 | (2018.01) |

(52) U.S. Cl.
CPC ....... *G01N 23/201* (2013.01); *G01N 33/4833* (2013.01); *G06F 21/602* (2013.01); *G06N 3/08* (2013.01); *G06Q 20/085* (2013.01); *G06Q 20/325* (2013.01); *G16H 10/40* (2018.01); *G16H 10/60* (2018.01); *G16H 30/20* (2018.01); *G16H 40/63* (2018.01); *G16H 40/67* (2018.01); *G01N 2223/0566* (2013.01); *G01N 2223/6126* (2013.01)

(58) Field of Classification Search
CPC ........ G16H 50/30; A61B 5/00; A61B 5/4312; G01N 23/20; G01N 23/201; G01N 33/4833; G01N 2223/0566; G01N 2223/6126; G06F 21/602; G06F 21/6245; G06N 3/08; G06N 3/04; G06N 20/00; G06Q 20/085; G06Q 20/325
See application file for complete search history.

(56) References Cited

U.S. PATENT DOCUMENTS

| | | | |
|---|---|---|---|
| 6,483,891 | B1 | 11/2002 | Lazarev et al. |
| 9,492,130 | B2 | 11/2016 | Flagle et al. |
| 2003/0014418 | A1 | 1/2003 | Adler et al. |
| 2006/0014265 | A1 | 1/2006 | Ferrari et al. |
| 2006/0015265 | A1 | 1/2006 | Raich |
| 2007/0032832 | A1 | 2/2007 | Feher |
| 2014/0257135 | A1* | 9/2014 | DeFreitas ............... G01N 35/04 600/566 |
| 2014/0287937 | A1* | 9/2014 | So ....................... C12Q 1/6855 435/6.12 |
| 2015/0269323 | A1 | 9/2015 | Ginsburg |
| 2016/0235372 | A1 | 8/2016 | Schneider et al. |
| 2017/0362585 | A1 | 12/2017 | Wang et al. |
| 2018/0038845 | A1 | 2/2018 | Zimmermann et al. |
| 2018/0122499 | A1 | 5/2018 | Austin et al. |
| 2019/0113451 | A1 | 4/2019 | Weissleder et al. |
| 2019/0372978 | A1 | 12/2019 | Vendrell et al. |
| 2020/0098476 | A1 | 3/2020 | Loscutoff et al. |
| 2022/0008027 | A1 | 1/2022 | Lazarev et al. |
| 2022/0013227 | A1 | 1/2022 | Lazarev et al. |
| 2022/0013233 | A1 | 1/2022 | Lazarev et al. |
| 2022/0044401 | A1 | 2/2022 | Chennubhotla et al. |
| 2022/0415505 | A1 | 12/2022 | Lazarev et al. |

FOREIGN PATENT DOCUMENTS

| | | |
|---|---|---|
| KR | 20180076702 A | 7/2018 |
| KR | 101931754 B1 | 12/2018 |
| WO | 2021257451 A1 | 12/2021 |
| WO | 2021257457 A1 | 12/2021 |

OTHER PUBLICATIONS

James, "Fiber diffraction of skin and nails provides an accurate diagnosis of malignancies", Int. J. Cancer: 125, 133-138, 13 pages, Jul. 2009.

Ortiz et al., "Biomarkers of disease in human nails: a comprehensive review", Critical Reviews in Clinical Laboratory Sciences, Oct. 7, 2021, 18 pgs, Taylor & Francis Group.

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, "Written Opinion of the International Searching Authority" in connection with related International Application No. PCT/US2021/037238, dated Oct. 5, 2021, 5 pgs.

Rodriguez, Kari, Authorized Officer, Commissioner for Patents, U.S. Patent and Trademark Office, "International Search Report" in connection with related International Application No. PCT/US2021/037224, dated Sep. 29, 2021, 3 pgs.

Rodriguez, Kari, Authorized Officer, Commissioner for Patents, U.S. Patent and Trademark Office, "Written Opinion of the International Searching Authority" in connection with related International Application No. PCT/US2021/037224, dated Sep. 29, 2021, 6 pgs.

EP21826034.7 Extended European Search Report dated May 15, 2024.

European Search Report dated May 24, 2024 for European Patent Office Patent Application No. 21826535.3.

Fagundes, et al., Structural Characterization of Canine Mammary Tissue by X-Ray Diffraction. Radiation Physics and Chemistry 155(1):1-13 (2019).

Ghammraoui, Bahaa, et al. Maximum-likelihood Estimation Of Scatter Components Algorithm For X-ray Coherent Scatter Computed Tomography Of The Breast. Physics in Medicine and Biology. vol. No. 61, Issue No. 8: 3164-3179 (2016).

Graewert, Melissa A, et al. Impact And Progress In Small And Wide Angle X-ray Scattering (SAXS and WAXS). Current Opinion in Structural Biology. vol. No. 23, Issue No. 5: 748-754 (2013).

Lazarev, Pavel, et al. Human Tissue X-ray Difrraction: Breast, Brain, and Prostate, IEEE Proceedings of the 22nd Annual EMBS International Conference. vol. 4: 3230-3231 (2000).

Sidhu, Small Angle X-Ray Scattering as a Diagnostic Tool for Breast Cancer. School of Physics 1-302 (2009).

Sidhu, S., et al. Classification of breast tissue using a laboratory system for small-angle x-ray scattering (SAXS). Phys. Med. Biol. 56(21):6779-6791 (2011).

U.S. Appl. No. 17/448,886 Notice of Allowance dated May 20, 2024.

U.S. Appl. No. 17/448,886 Office Action dated Feb. 26, 2024.

U.S. Appl. No. 17/448,887 Notice of Allowance dated May 15, 2024.

U.S. Appl. No. 17/448,887 Office Action dated Nov. 27, 2023.

U.S. Appl. No. 17/448,888 Office Action dated Mar. 22, 2023.

U.S. Appl. No. 17/593,846 Office Action dated Feb. 6, 2023.

\* cited by examiner

Laboratory X-ray diffraction equipment

Figure 1.3: The levels of arrangement in fibrillar collagen in breast tissue. Typical dimensions taken from Fernandez et al. [51] (Printed with permission from Dr. M Fernandez, 2009)

FIG. 3A    FIG. 3B
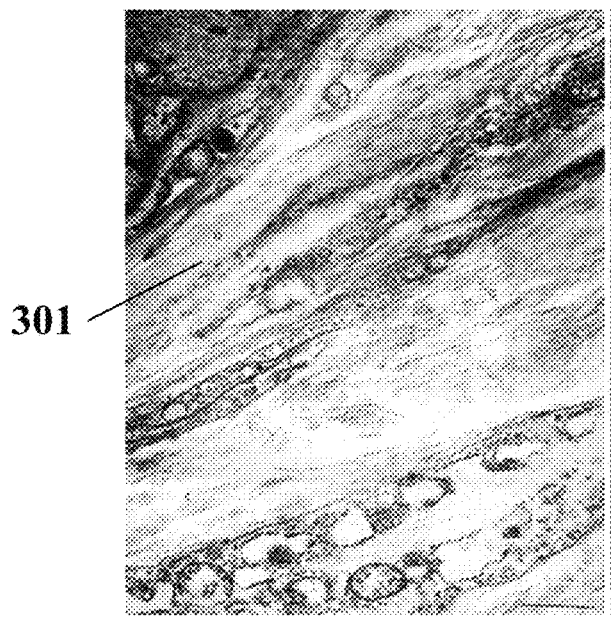 
301    302
(a)    (b)
Figure 1.5: Electron micrographs of collagen tissue in (a) normal tissue and (b) invasive carcinoma tissue. In the normal tissue, the in-tact collagen fibres are aligned and well structured, where the collagen strands in the invasive carcinoma are broken and unstructured. (Printed with permission from Oxford University Press 2009. [96])

a SAXS pattern from a normal breast tissue biopsy a SAXS pattern from breast tissue with a known disease a SAXS pattern from breast tissue with a known disease

DIFFRACTION-BASED GLOBAL IN VITRO DIAGNOSTIC SYSTEM

CROSS-REFERENCE

The present application claims the benefit of U.S. Provisional Patent Application No. 63/039,340, filed Jun. 15, 2020, which is herein incorporated by reference in its entirety.

BACKGROUND

Pathological analysis of in vitro tissue samples, e.g., biopsy samples, is an expensive, labor intensive, and time-consuming process which is primarily based on human assessment of the visual appearance of the samples. Furthermore, the sample preparation required for visual assessment is also a labor intensive and time-consuming process which may lead to erroneous results in the subsequent analysis. The final analysis of the samples is based on visual assessment by a trained professional, and thus relies on human judgement and is therefore subjective by nature.

SUMMARY

Applicant has recognized a need for better pathological analysis and diagnostic tools, e.g., in vitro analytical methods for reliable and early detection and diagnosis of cancer and other diseases. Disclosed herein are novel methods and systems for fast and accurate in vitro analysis of tissue samples that utilize an objective digital measurement of the structural properties of tissue in the sample, which is directly indicative of its physiological and pathological status.

An aspect of the present disclosure provides a system comprising: (a) one or more diffraction apparatus operatively coupled to a computer database over a network, wherein the one or more diffraction apparatus are configured to collect sample data comprising diffraction pattern data for in vitro samples and transfer the sample data, or data derived therefrom, to the computer database over the network; and (b) one or more computer processors operatively coupled to the one or more diffraction apparatus, wherein the one or more computer processors are individually or collectively configured to: (i) receive the sample data, or data derived therefrom, from at least one of the one or more diffraction apparatus; (ii) transmit the sample data, or data derived therefrom, from at least one of the one or more diffraction apparatus to the computer database; and (iii) process the sample data, or data derived therefrom, for an individual in vitro sample using a data analytics algorithm that provides a computer-aided diagnostic indicator for the in vitro sample or for a subject from which the in vitro sample was derived.

In some embodiments, the system further comprises a user interface that allows an individual subject or a healthcare provider to upload the individual subject's sample data for an in vitro sample to the computer database in exchange for processing of the sample data to receive the computer-aided diagnostic indicator for the in vitro sample or for the individual subject. In some embodiments, the user interface is further configured to allow an individual subject or their healthcare provider to make payments or upload an individual subject's signed consent form. In some embodiments, the system further comprises two or more diffraction apparatus located in two or more different geographic locations. In some embodiments, the one or more diffraction apparatus comprise a data encryption device that includes a global positioning system (GPS) positioning sensor and generates encrypted sample data, and when transferred to the computer database the encrypted sample data is used to track changes in location of the one or more diffraction apparatus. In some embodiments, the one or more diffraction apparatus are configured to perform small angle X-ray scattering (SAXS) measurements. In some embodiments, the one or more diffraction apparatus are configured to perform wide angle X-ray scattering (WAXS) measurements. In some embodiments, the in vitro samples comprise a surgical sample, a resection sample, a pathology sample, a biopsy sample, or any combination thereof. In some embodiments, the sample data further comprises pathology lab image data, subject data, or any combination thereof. In some embodiments, the computer database resides on a central server. In some embodiments, the computer database resides in the cloud. In some embodiments, the sample data transferred to the computer database are depersonalized prior to the transfer. In some embodiments, a key for mapping the depersonalized sample data stored in the computer database to an individual subject is stored in a local institutional database or in the individual subject's personal files. In some embodiments, the data analytics algorithm comprises a statistical analysis of diffraction pattern data or a function thereof. In some embodiments, the statistical analysis comprises determination of a pair-wise distance distribution function, determination of a Patterson function, a calculation of a Porod invariant, a cluster analysis, a dispersion analysis, determination of one or more molecular structural periodicities, or any combination thereof. In some embodiments, the statistical analysis comprises a determination of a structural periodicity of collagen. In some embodiments, the statistical analysis comprises a determination of a structural periodicity of one or more lipids. In some embodiments, the statistical analysis comprises a determination of a structural periodicity of a tissue. In some embodiments, the data analytics algorithm comprises a machine learning algorithm. In some embodiments, the machine learning algorithm comprises a supervised learning algorithm, an unsupervised learning algorithm, a semi-supervised learning algorithm, a reinforcement learning algorithm, a deep learning algorithm, or any combination thereof. In some embodiments, the machine learning algorithm is a deep learning algorithm. In some embodiments, the deep learning algorithm is a convolutional neural network, a recurrent neural network, or a recurrent convolutional neural network. In some embodiments, the machine learning algorithm is trained using a training dataset comprising pathology lab image data, diffraction pattern data, subject data, or any combination thereof from one or more control samples. In some embodiments, the training dataset is updated as new sample data are uploaded to the computer database. In some embodiments, the sample data further comprises subject data comprising an individual subject's age, sex, ancestry data, genetic data, behavioral data, or any combination thereof, wherein the sample is from the individual subject. In some embodiments, the computer-aided diagnostic indicator for the in vitro sample comprises an indicator of a likelihood that the sample is positive or negative for a cancer. In some embodiments, the cancer comprises breast cancer, brain cancer, bone cancer, lung cancer, cervical cancer, bladder cancer, head and neck cancer, kidney cancer, intestinal cancer, liver cancer, ovarian cancer, pancreatic cancer, prostate cancer, skin cancer, throat cancer, oral cancer, vaginal cancer, or any combination thereof. In some embodiments, the pathology lab image data comprises micrographs of stained in vitro tissue specimens. In some embodiments, the system is used to monitor the efficacy of a cancer therapeutic treatment.

Another aspect of the present disclosure provides a method comprising: a) using one or more diffraction apparatus to acquire sample data comprising diffraction pattern data for in vitro samples, wherein the one or more diffraction apparatus are operatively coupled to a computer database over a network and are configured to transfer the sample data, or data derived therefrom to the computer database over the network; b) using one or more computer processors operatively coupled to the one or more diffraction apparatus to: (i) receive the sample data, or data derived therefrom, from at least one of the one or more diffraction apparatus; (ii) transmit the sample data, or data derived therefrom, from at least one of the one or more diffraction apparatus to the computer database; and (iii) process the sample data, or data derived therefrom, for an individual in vitro sample using a data analytics algorithm that provides a computer-aided diagnostic indicator for the in vitro sample or for a subject from which the in vitro sample was derived.

In some embodiments, the method further comprises providing a user interface that allows an individual subject or a healthcare provider to upload the individual subject's sample data to the computer database in exchange for processing of the sample data to receive the computer-aided diagnostic indicator for the in vitro sample or for the individual subject. In some embodiments, the user interface is further configured to allow the individual subject or the healthcare provider to make payments or upload a signed consent form for use of the sample data. In some embodiments, the one or more diffraction apparatus comprise a plurality of diffraction apparatus located in different geographic locations. In some embodiments, the one or more diffraction apparatus comprise a data encryption device that includes a global positioning system (GPS) positioning sensor and generates encrypted data, and when transferred to the computer database the encrypted data is used to track changes in locations of the one or more diffraction apparatus. In some embodiments, the one or more diffraction apparatus are configured to perform small angle X-ray scattering (SAXS) measurements. In some embodiments, the one or more diffraction apparatus are configured to perform wide angle X-ray scattering (WAXS) measurements. In some embodiments, the sample data further comprises pathology lab image data, subject data, or any combination thereof. In some embodiments, the computer database resides on a central server. In some embodiments, the computer database resides in the cloud. In some embodiments, the sample data are depersonalized prior to the transfer. In some embodiments, a key for mapping the depersonalized sample data stored in the computer database to an individual subject is stored in a local institutional database or in the individual subject's personal files. In some embodiments, the data analytics algorithm comprises a statistical analysis of diffraction pattern data or a function thereof. In some embodiments, the statistical analysis comprises determination of a pair-wise distance distribution function, determination of a Patterson function, a calculation of a Porod invariant, a cluster analysis, a dispersion analysis, determination of one or more molecular structural periodicities, or any combination thereof. In some embodiments, the statistical analysis comprises a determination of a structural periodicity of collagen. In some embodiments, the statistical analysis comprises a determination of a structural periodicity of a lipid. In some embodiments, the statistical analysis comprises a determination of a structural periodicity of a tissue. In some embodiments, the data analytics algorithm comprises a machine learning algorithm. In some embodiments, the machine learning algorithm comprises a supervised learning algorithm, an unsupervised learning algorithm, a semi-supervised learning algorithm, a reinforcement learning algorithm, a deep learning algorithm, or any combination thereof. In some embodiments, the machine learning algorithm is a deep learning algorithm. In some embodiments, the deep learning algorithm is a convolutional neural network, a recurrent neural network, or a recurrent convolutional neural network. In some embodiments, the machine learning algorithm is trained using a training dataset comprising pathology lab image data, diffraction pattern data, subject data, or any combination thereof from one or more control samples. In some embodiments, the training dataset is updated as new sample data are uploaded to the computer database. In some embodiments, the sample data further comprises subject data comprising an individual subject's age, sex, ancestry data, genetic data, behavioral data, or any combination thereof. In some embodiments, the computer-aided diagnostic indicator for the in vitro sample comprises an indicator of the likelihood that the sample is positive or negative for a cancer. In some embodiments, the cancer comprises breast cancer, brain cancer, bone cancer, lung cancer, cervical cancer, bladder cancer, head and neck cancer, kidney cancer, intestinal cancer, liver cancer, ovarian cancer, pancreatic cancer, prostate cancer, skin cancer, throat cancer, oral cancer, vaginal cancer, or any combination thereof. In some embodiments, the pathology lab image data comprises micrographs of stained in vitro tissue specimens. In some embodiments, the method further comprises collecting different in vitro samples from an individual subject at different time points, and repeating a)-b) at the different time points to monitor a change over time of a condition, disease, or disorder associated with the individual subject upon a determination of the individual sample as being positive for the condition, disease, or disorder. In some embodiments, the different time points are within a time period during which the individual subject is subjected to a treatment or a therapeutic intervention. In some embodiments, the method further comprises determining an efficacy of the treatment or the therapeutic intervention. In some embodiments, the in vitro samples comprise a tissue sample. In some embodiments, the in vitro samples comprise a surgical sample, a resection sample, a pathology sample, a biopsy sample, or any combination thereof.

Another aspect of the present disclosure provides a non-transitory computer readable medium comprising machine executable code that, upon execution by one or more computer processors, implements any of the methods described above or disclosed elsewhere herein.

Another aspect of the present disclosure provides a system comprising one or more computer processors and computer memory coupled thereto. The computer memory comprises machine executable code that, upon execution by the one or more computer processors, implements any of the methods described above or disclosed elsewhere herein.

Additional aspects and advantages of the disclosed concepts will become readily apparent to those skilled in the art upon review of the following detailed description, wherein only illustrative embodiments of the disclosed concepts are shown and described. As will be realized, the concepts of the present disclosure may be implemented in other and different embodiments, and the several details thereof are amenable to modification in various obvious respects, all without departing from the scope of the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A: schematic illustration of an x-ray diffraction experiment. FIG. 1B: schematic illustration of small angle x-ray scattering (SAXS) and wide-angle x-ray scattering (WAXS) by a sample comprising molecular periodicities. FIG. 1C: illustration of a laboratory x-ray diffractometer.

FIGS. 3A-3B show examples of collagen in normal tissue (FIG. 3A) and in invasive carcinoma tissue (FIG. 3B) (from: "Small Angle X-Ray Scattering as a Diagnostic Tool for Breast Cancer", Sabeena Sidhu, BSc, MSc School of Physics, Monash University, Feb. 12, 2009).

FIG. 5A: a SAXS pattern from a normal breast tissue biopsy. FIG. 5B: a SAXS pattern from a biopsy of diseased breast tissue.

FIG. 6A: a SAXS pattern from a biopsy of diseased breast tissue. FIG. 6B: a plot of scattering intensity as a function of q value.

DETAILED DESCRIPTION

Figure 1A:
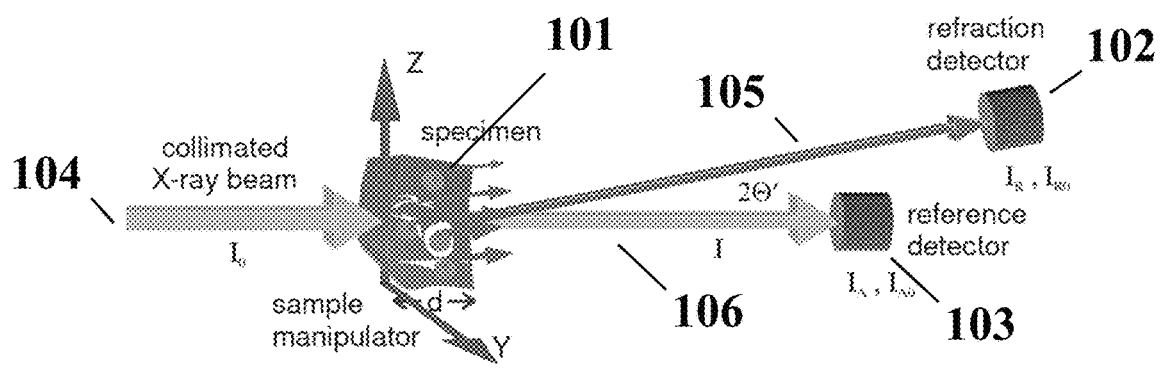
FIGS. 1A-1C show an overview of x-ray diffraction methodology.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Systems and methods for providing a computer-aided diagnostic indicator for a subject are disclosed. The systems may comprise a plurality of diffraction apparatus operably coupled to a computer database over a network, where the diffraction apparatus are configured to acquire small-angle x-ray scattering and/or wide-angle x-ray scattering data for an in vitro tissue sample derived from a subject. Optionally, the diffraction apparatus may also be configured to acquire absorptive images of the tissue. The system is configured to collect and process diffraction data, image data, and/or other data pertinent to the subject using a data analytics algorithm to provide a computer-aided diagnostic indicator for the subject. The data analytics algorithm is randomly, periodically, or continually updated and refined using the data for a plurality of subjects stored in the computer database. In some instances, the computer-aided diagnostic indicator may comprise an indicator of the likelihood that the in vitro tissue sample is cancerous (or diseased) or that the subject from which the tissue sample was derived has cancer (or some other disease). In some instances, the computer-aided diagnostic indicator may comprise a diagnosis that the in vitro tissue sample is cancerous (or diseased) or that the subject from which the tissue sample was derived has cancer (or some other disease).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Unless otherwise defined, the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term "diffraction apparatus" generally refers to an instrument or diffractometer configured to record diffraction data from one or more in vitro tissue samples or specimens. The diffraction apparatus may be an x-ray diffractometer. In some instances, the diffraction apparatus may be configured to record diffraction data and image data.

As used herein, the term "computer-aided diagnostic indicator" generally refers to an indicator comprising diagnostic information generated with the help of one or more computer processors. In some instances, the "computer-aided diagnostic indicator" may comprise a probability score for the likelihood that an in vitro tissue sample is cancerous (or diseased), or that the subject from which the tissue sample was derived has cancer, e.g., breast cancer (or some other disease). In some instances, the "computer-aided diagnostic indicator" may comprise a diagnosis that an in vitro tissue sample is cancerous (or diseased), or that the subject from which the tissue sample was derived has cancer, e.g., breast cancer (or some other disease).

As used herein, the term "subject" generally refers to an animal, such as a mammal A subject may be a human or non-human mammal A subject may be afflicted with a disease or suspected of being afflicted with or having a disease. The subject may not be suspected of being afflicted with or having the disease. The subject may be symptomatic. Alternatively, the subject may be asymptomatic. In some cases, the subject may be treated to alleviate the symptoms of the disease or cure the subject of the disease. A subject may be a patient undergoing treatment by a healthcare provider.

As used herein, the term "healthcare provider" generally refers to a medical practitioner or support staff. The healthcare provider may be a doctor, a nurse, a dentist, a technician, a student, or the like. The healthcare provider may be at least partially responsible for the healthcare of the subject.

As used herein, the term "institution" generally refers to an entity related to one or more healthcare providers. The institution may be a medical center, a doctor's office, a clinic, a hospital, a university, or the like.

As used herein, the term "cancer" generally refers to a proliferative disorder caused or characterized by a proliferation of cells which have lost susceptibility to normal growth control. Cancers of the same tissue type usually originate in the same tissue and may be divided into different subtypes based on their biological characteristics. Non-limiting examples of categories of cancer are carcinoma (epithelial cell derived), sarcoma (connective tissue or mesodermal derived), leukemia (blood-forming tissue derived) and lymphoma (lymph tissue derived). Cancer may involve every organ and tissue of the body. Specific examples of cancers that do not limit the definition of cancer may include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. In some cases, a cancer can be multicentric. In some cases, a cancer can be a cancer of unknown primary (CUP).

As used herein, the term "cloud" generally refers to shared or sharable storage of electronic data, e.g., a distributed network of computer servers. In some instances, the cloud may be used for archiving electronic data, sharing electronic data, and analyzing electronic data.

The methods and systems described herein are applied to characterization of tissues in vitro, that is, samples or specimens that have been collected from or removed from a subject such as a patient. As used herein, the terms "sample" or "specimen" are used interchangeably and may refer to any of a variety of in vitro tissue samples known to those of skill in the art including, but not limited to, surgical samples or specimens, surgical resection samples or specimens, biopsy samples or specimens, blood sample, and the like.

Diffraction-based systems and methods of use: In one aspect, the present disclosure provides a system that outputs a computer-aided diagnostic indicator from an analysis of an in vitro tissue sample for a subject that may have or may be at risk for developing a disease, such as a proliferative disease or cancer. In one aspect, the computer-aided diagnostic indicator for the subject is based on an analysis of diffraction (or scattering) data for an in vitro tissue specimen derived from the subject. The system may comprise one or more diffraction apparatus operatively coupled to a computer database over a network. A diffraction apparatus of the one or more diffraction apparatus may be configured for transfer of image data, diffraction pattern data, subject data, or any combination thereof to the computer database over the network. The system may comprise one or more computer processors operatively coupled to the one or more diffractometers. The one or more computer processors may be individually or collectively configured to (i) receive the image data, diffraction pattern data, subject data, or any combination thereof from the one or more diffraction apparatus; (ii) transmit the image data, diffraction pattern data, subject data, or any combination thereof to the computer database; and (iii) process the image data, diffraction pattern data, subject data, or any combination thereof for in vitro tissue samples from an individual subject using a data analytics algorithm that provides a computer-aided diagnostic indicator for the individual subject.

In another aspect, the present disclosure provides a method for generating a computer-aided diagnostic indicator for a subject that may have or may be at risk for developing a disease, such as a proliferative disease or cancer. The method may comprise acquiring data comprising image data, diffraction pattern data, subject data, or any combination thereof for an in vitro tissue sample derived from an individual subject using one of a plurality of diffraction apparatus operatively coupled to a computer database over a network. The plurality of diffraction apparatus may be configured for transfer of the data to the computer database over the network. One or more computer processors may be operatively coupled to the plurality of diffraction apparatus. The one or more computer processors may be used to receive the data comprising image data, diffraction pattern data, subject data, or any combination thereof from the plurality of diffraction apparatus that are operatively coupled to a computer database over the network and may be configured for transfer of the data comprising the image data, diffraction pattern data, subject data, or any combination thereof to the computer database over the network. The data comprising the image data, diffraction pattern data, subject data, or any combination thereof may be transmitted to the computer database. The data comprising the image data, diffraction pattern data, subject data, or any combination thereof may be processed for the individual tissue sample using a data analytics algorithm that may provide a computer-aided diagnostic indicator for the individual tissue sample or for the subject from which the tissue sample was derived. The following description may relate to both the method and the system.

In some instances, the one or more diffraction apparatus may be diffraction apparatus as described elsewhere herein.

The one or more diffraction apparatus may be stand-alone diffraction apparatus (e.g., instruments or components of a system that do not comprise other functionalities). The one or more diffraction apparatus may be coupled with other instruments. The operative coupling to a computer database may be over a local network (e.g., a local area network (LAN)) or a remote network (e.g., the internet).

In some instances, the image data may be images (e.g., micrographs of stained in vitro tissue samples), image metadata, or the like, or any combination thereof. The images may be raw images (e.g., images as captured from a detector such as a CCD camera), processed images (e.g., images that have had one or more processing operations performed), image analogues (e.g., matrices of intensity values corresponding to pixels, vector representations of images), or the like. The image metadata may comprise non-image information regarding the conditions under which the image was acquired (e.g., tissue sample processing protocol, tissue sample stain, microscope settings, CCD camera exposure time, date and time of acquisition, ambient conditions, etc.). In some instances, the image data do not include in-situ image data (e.g., mammography images).

In some instances, the diffraction pattern data may comprise diffraction patterns, diffraction pattern metadata, or the like, or any combination thereof. The diffraction patterns may comprise diffraction patterns generated from an interaction of a radiation beam (e.g., an x-ray beam, a neutron beam) with a tissue. The diffraction patterns may comprise raw diffraction patterns, processed diffraction patterns, diffraction pattern analogues, or the like. The diffraction pattern metadata may comprise metadata as described elsewhere herein.

In some instances, the image data and/or diffraction pattern data may comprise data taken from both a healthy tissue sample and a tissue sample suspected of having an abnormality. In some instances, both the healthy tissue sample and the tissue sample suspected of having an abnormality may be derived from the same subject. For example, diffraction data can be taken from both a biopsy sample from subject's breast suspected of having a cancer as well as a biopsy sample from the subject's other breast that is suspected of being free from the cancer.

In some instances, the subject data may comprise an individual subject's age, sex, ancestry data, genetic data, behavioral data, medical history, previous medical tests or diagnostics, occupational data, social determinants of health, or any combination thereof. The ancestry data may be determined by one or more genetic tests. The ancestry data may comprise ancestry data reported by the subject. The genetic data may comprise genetic abnormalities, predispositions, or the like. For example, the subject data may comprise information regarding a subject's genetic predisposition to breast cancer (e.g., the presence or absence of a breast cancer gene).

In some instances, the computer database may be a cloud-based database, e.g., a database that resides on one more remote computer servers. In some instances, the computer database may be a local computer database (e.g., a computer connected to a diffraction apparatus).

In some instances, the one or more computer processors may be computer processors that are part of one or more computer servers that host the computer database. In some instances, the one or more computer processors may be computers operatively coupled to the one or more diffraction apparatus (e.g., computers controlling the one or more diffractometers). The receiving of image data may comprise real-time or substantially real-time receipt of the image data.

For example, in some instances, a stream of image data can be transmitted from a diffraction apparatus to the one or more computer processors as the images are being taken. In some instances, the image data may be transmitted in packets (e.g., bundles of one or more images). For example, a series of images of a plurality of subjects can be taken throughout a day and can then be all transmitted together. In another example, all images taken of a single subject during a single scan or single session can be transmitted together. The transmitting to the computer database may be real-time transmitting, substantially real-time transmitting, intermittent transmitting (e.g., transmitting packets), or any combination thereof.

In some instances, diffraction data processing and/or image data processing may occur between the receiving of the diffraction and/or image data and the transmitting of image data. For example, in some instances, the one or more computer processors may be configured to compress the diffraction and/or image data to improve the transfer speed to the database. In another example, the one or more computer processors can be configured to extract relevant parameters (e.g., d spacings, pair distribution functions) from the data (e.g., diffraction pattern data) before transmitting to the computer database, thereby significantly decreasing the amount of data to be transmitted. In some instances, the processing of diffraction and/or image data may be performed after the data has been transferred to the computer database. The processing of the diffraction and/or image data may be local processing (e.g., processing on a computer local to the diffraction apparatus) or remote processing (e.g., processing on a remote computer server or cloud-based server). In some instances, the data processing may comprise the application of a statistical analysis and/or machine learning algorithm (which individually or collectively may be referred to as a "data analytics algorithm" herein). The data processing may comprise processing diffraction data and/or image data for a single tissue sample or a plurality of tissue samples. For example, the diffraction and/or image data acquired for a single tissue sample can be processed to generate the computer-aided diagnostic indicator for the sample. In another example, diffraction data and/or image data from a plurality of tissue samples may be processed to refine the data analytics algorithm and/or to generate a baseline diagnostic indicator.

In some instances, the system may further comprise a user interface. The user interface may be configured to allow an individual subject and/or their healthcare provider to upload the individual subject's image data, diffraction pattern data, subject data, or any combination thereof to the computer database. The uploading the individual subject's image data, diffraction pattern data, subject data, or any combination thereof to the computer database may be in exchange for processing the individual subject's image data, diffraction pattern data, or any combination thereof to receive the computer-aided diagnostic indicator for the individual subject. For example, a healthcare provider can use the user interface to upload diffraction images of a suspicious mass identified in a mammogram, along with pathology laboratory micrographs of stained breast biopsy specimens, to the computer database. In this example, the system comprising the one or more computer processors and the computer database can then process the diffraction images, as well as the micrograph images, using a data analytics algorithm to generate a diagnostic indicator that is provided to the healthcare provider. In some instances, the diffraction images and the micrograph images may be retained on the computer database, where they can be used to refine the data analytics algorithm that generates the diagnostic indicator. The user interface may be configured to allow an individual subject and/or their healthcare provider to make payments and/or upload the individual subject's signed consent form. The payments may be cash payments (e.g., the user interface displays an address to send the payments), check payments (e.g., paper or electronic check payments), card payments (e.g., credit or debit card payment processing), app-based payments (e.g., PayPal®, Venmo®), cryptocurrency payments (e.g., Bitcoin), or any combination thereof. For example, in some instances, an individual subject may pay via a health savings account debit card. The signed consent form may be signed by the individual subject and/or the healthcare provider. The signed consent form may be related to the computer-aided diagnostic indicator. For example, the individual subject can sign and upload a consent form stating that the subject's diffraction and/or image data may be retained on the computer database. In some instances, the signed consent form may be physically signed, electronically signed, or any combination thereof.

In some instances, a system of the present disclosure may comprise 1, 2, 3, 4, 5, 6, 7, 8, 9, 10, 20, 30, 40, 50, 60, 70, 80, 90, 100, 150, 200, 250, 300, 350, 400, 450, 500, or more than 500 diffraction apparatuses. In some instances, a system of the present disclosure may comprise at most about 500, 450, 400, 350, 300, 250, 200, 150, 100, 90, 80, 70, 60, 50, 40, 30, 20, 10, 9, 8, 7, 6, 5, 4, 3, 2, or fewer than 2 diffraction apparatuses. In some instances, the number of diffraction apparatus in the system may range between any two of the values specified in this paragraph. For example, in some instances, the number of diffraction apparatus in the system may range from 4 to 100. Those of skill in the art will recognize that in some instances, the number of diffraction apparatus in the system may have any value within the range of values specified in this paragraph, e.g., 125 diffraction apparatus.

The one or more diffraction apparatus may be two or more diffraction apparatus located in two or more different geographic locations. For example, a first diffraction apparatus in a first location can send one set of image data to the one or more computer processors while a second diffraction apparatus in a second location can send one set of diffraction pattern data to the one or more computer processors. In this example, the image data and the diffraction pattern data can both be used to refine the data analytics algorithm that generates computer-aided diagnostic indicators for individual samples and may also both be retained on the computer database. The one or more diffraction apparatus may comprise a data encryption device. The data encryption device may comprise a global positioning system (GPS) positioning sensor. The data encryption device may generate encrypted image data, diffraction pattern data, subject data, or any combination thereof. The encrypted image data, diffraction pattern data, subject data, or any combination thereof may be transferred to the computer database. The encrypted image data, diffraction pattern data, subject data, or any combination thereof may comprise data regarding changes in a location of the one or more diffraction apparatus. For example, the image metadata generated by a diffraction apparatus can comprise location information for that diffraction apparatus. In this example, a movement of the diffraction apparatus can be tracked using the image metadata transmitted by the diffraction apparatus. In another example, the GPS positioning sensor can be in constant communication with the computer database regarding the location of the diffraction apparatus. The inclusion of the GPS sensor may reduce a likelihood that the diffraction apparatus is stolen or misappropriated by untrained users. The data encryption device may be configured to encrypt the data in line with a health data privacy standard. For example, the encryption device may make the transmission and storage of the image data, diffraction pattern data, subject data, or any combination thereof compliant with the Health Insurance Portability and Accountability Act (HIPAA). The data encryption device may comprise a module configured to only permit communication between the diffraction apparatus and the computer database. For example, other network communications can be disabled such that the data from the diffraction apparatus can be sent only to the computer database.

In some instances, the plurality of diffraction apparatus that are operatively coupled to the system may be located in 2, 3, 4, 5, 6, 7, 8, 9, 10, 20, 30, 40, 50, 60, 70, 80, 90, 100, 150, 200, 250, 300, 350, 400, 450, 500, or more than 500 different geographical locations (thereby effectively constituting a global diagnostics system). In some instances, the number of different geographical locations comprising diffraction apparatus that are operatively coupled to the system may range between any two of the values specified in this paragraph. For example, in some instances, the number of different geographical locations included in the system may range from 8 to 20. Those of skill in the art will recognize that in some instances, the number of different geographical locations included in the system may have any value within the range of values specified in this paragraph, e.g., 14 different geographical locations.

Small angle x-ray scattering: In some instances, the one or more diffraction apparatus may be configured to perform small angle x-ray scattering (SAXS) measurements. The SAXS measurements may comprise measurements of the long-range ordering of the tissue. For example, the SAXS measurement can record measurements of tissue order in the range of 10 to 1,000 nanometers. The SAXS measurements may comprise measurements of scattering of at least about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.6, 7, 7.5, 8, 8.5, 9, 9.5, 10, or more degrees. The SAXS measurements may comprise measurements of at most about 10, 9.5, 9, 8.5, 8, 7.5, 7, 6.5, 6, 5.5, 5, 4.5, 4, 3.5, 3, 2.5, 2, 1.5, 1, 0.9, 0.8, 0.7, 0.6, 0.5, 0.4, 0.3, 0.2, 0.1, 0.05, 0.01, or less degrees. The SAXS measurements may comprise measurements of a range as defined by any two of the proceeding numbers. For example, the SAXS measurements may comprise measurements of scattering of 0.1-10 degrees. The SAXS measurements may comprise measurements with respect to degrees (e.g., $\Theta$), $2\Theta$, d (e.g., distance measured in Angstroms), q (e.g., 1/d), or the like, or any combination thereof.

Wide angle x-ray scattering: In some instances, the one or more diffraction apparatus may be configured to perform wide angle x-ray scattering (WAXS) measurements. The WAXS measurements may comprise measurements of the short-range ordering of the tissue. For example, the WAXS measurements can record measurements of the tissue order below 10 nanometers. The WAXS measurements may provide structural information about non-tissue objects in the tissue. For example, a WAXS measurement of an object suspected of being a breast calcification can confirm that the object is composed of calcium oxalate and calcium phosphate. In another example, a WAXS measurement can generate information regarding a molecular structure within a tissue. The WAXS measurements may comprise measurements of at least about 10, 15, 20, 25, 30, 35, 40, 45, or more degrees. The WAXS measurements may comprise measurements of at most about 45, 40, 35, 30, 25, 20, 15, 10, or less degrees. The WAXS measurements may comprise measurements of a range as defined by any two of the proceeding numbers. For example, the WAXS measurements can comprise measurements of scattering of 10-45 degrees. The WAXS measurements may comprise measurements with respect to degrees (e.g., $\Theta$), $2\Theta$, d (e.g., distance measured in Angstroms), q (e.g., 1/d), or the like, or any combination thereof.

Computer database: As noted above, in some instances, the computer database may reside on a central computer server. In some instances, the central computer server may reside in the cloud (e.g., may be a cloud-based computer server comprising a distributed network of remote computer servers). In some instances, the computer database may reside on a local server. In some instances, data may be transferred or exchanged between a local computer database and a remote or central computer database. The computer database may reside on a privacy law compliant server (e.g., a HIPAA complaint server).

In some instances, the image data, diffraction pattern data, subject data, or any combination thereof transferred to the computer database may be depersonalized before transfer. The depersonalization may comprise removal of personally identifiable information (e.g., name, patient number, social security number, address, etc.). For example, identifying information can be removed from image metadata and/or subject data before the image metadata and/or subject data are transferred to the computer database. The depersonalization of the image data, diffraction pattern data, subject data, or any combination thereof may aid in making the computer database compliant with privacy laws. In some instances, a key for mapping depersonalized image data, diffraction pattern data, subject data, or any combination thereof stored in the computer database to an individual subject may be stored in a local institutional database and/or in the individual subject's personal files. For example, a key can be generated that relates a subject to their depersonalized data for later reference or reunification. The local institutional database may be a database operated by the institution where the subject went to obtain the image data, diffraction pattern data, subject data, or any combination thereof. For example, a hospital can have a database comprising keys to link the identities of hospital patients to their depersonalized data. In another example, the key can be kept in the patient's personal medical files.

Data analytics algorithm: As noted above, in some instances the data analytics algorithm may comprise a statistical analysis of diffraction pattern data and/or a function thereof. In some instances, the data analytics algorithms may comprise a statistical analysis of image data, diffraction pattern data, subject data, a function of any of the proceeding, or any combination thereof. In some instances, the statistical analysis may comprise determination of a pairwise distance distribution function, determination of a Patterson function, a calculation of a Porod invariant, a cluster analysis, a dispersion analysis, determination of one or more molecular structural periodicities, or any combination thereof. The statistical analysis may comprise a determination of a structural periodicity of a tissue or a tissue feature. The structural analysis may comprise a determination of a structural periodicity of collagen, one or more lipids, or a combination thereof. For example, a diffraction pattern can provide information regarding the structural periodicity, and thus the relative degree of ordering, of the collagen within the spot size of the diffractometer. In another example, the ordering of lipid layers can be determined by diffraction, which can give information about the stiffness of the lipid layers and the chemical composition of the layers (e.g., the amount of cholesterol or other stiffening agents) on a local level. In some instances, the structural periodicity of the tissue may be used to determine a likelihood of a cancer being present within the tissue. For example, FIG. 3A shows an electron microscope image of normal collagen tissue, while FIG. 3B shows an electron microscope image of collagen in an invasive carcinoma tissue. In this example, the collagen in the normal tissue is more well-structured, which can give rise to stronger diffraction peaks, while the collagen in the carcinoma is poorly structured, which can result in weak diffraction peaks.

In some instances, the data analytics algorithm may comprise or further comprise the use of one or more machine learning algorithms. The one or more machine learning algorithms may be configured to operate upon image data, diffraction pattern data, subject data, or any combination thereof. The machine learning algorithm may comprise one or more supervised learning algorithms, one or more unsupervised learning algorithms, one or more semi-supervised learning algorithms, one or more reinforcement learning algorithms, one or more deep learning algorithms, or any combination thereof. The machine learning algorithm may be a deep learning algorithm. The deep learning algorithm may comprise one or more convolutional neural networks, one or more recurrent neural networks, and/or one or more recurrent convolutional neural networks.

Statistical analysis algorithms and/or machine learning algorithms implemented on a local computer or a remote server may be used to perform data analytics. For example, a machine learning algorithm can be configured to pre-process raw image data, diffraction pattern data, and/or subject data to remove noise or other artifacts. A different machine learning can be trained to identify features within the image data, diffraction pattern data, and/or subject data. Such a machine learning algorithm can cluster data points for use as an identification algorithm. Other machine learning algorithms can be configured to provide a computer-aided diagnostic indicator.

The machine learning algorithms may comprise a supervised, semi-supervised, or unsupervised machine learning algorithm. A supervised machine learning algorithm, for example, is an algorithm that is trained using labeled training data sets, e.g., data sets that comprise training inputs with known outputs. The training inputs can be provided to an untrained or partially trained version of the machine learning algorithm to generate a predicted output. The predicted output can be compared to the known output in an iterative process, and if there is a difference, the parameters of the machine learning algorithm can be updated. A semi-supervised machine learning algorithm is trained using a large set of unlabeled training data, e.g., unlabeled training inputs, and a small number of labeled training inputs. An unsupervised machine learning algorithm, e.g., a clustering algorithm, may find previously unknown patterns in data sets comprising data with no pre-existing labels.

One non-limiting example of a machine learning algorithm that can be used to perform some of the functions described above, e.g., processing of diffraction data, image data, and/or generating computer-aided diagnostic indicators, is a neural network. Neural networks employ multiple layers of operations to predict one or more outputs, e.g., a likelihood that a subject has cancer, from one or more inputs, e.g., image data, diffraction pattern data, subject data, processed data derived from image data, diffraction pattern data, and/or subject data, or any combination thereof. Neural networks can include one or more hidden layers situated between an input layer and an output layer. The output of each layer can be used as input to another layer, e.g., the next hidden layer or the output layer. Each layer of a neural network can specify one or more transformation operations to be performed on the data input to the layer. Such transformation operations may be referred to as "neurons". The output of a particular neuron may be, for example, a weighted sum of the inputs to the neuron, that is optionally adjusted with a bias and/or multiplied by an activation function, e.g., a rectified linear unit (ReLU) or a sigmoid function.

Training a neural network can involve providing inputs to the untrained neural network to generate predicted outputs, comparing the predicted outputs to expected outputs, and updating the algorithm's weights and biases in an iterative manner to account for the difference between the predicted outputs and the expected outputs. For example, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, such as obtaining a small magnitude of calculated cost.

Convolutional neural networks (CNNs) and recurrent neural networks can be used to classify or make predictions from image data, diffraction pattern data, subject data, or any combination thereof. CNNs are neural networks in which neurons in some layers, called convolutional layers, receive data from only small portions of a data set. These small portions may be referred to as the neurons' receptive fields. Each neuron in such a convolutional layer may have the same weights. In this way, the convolutional layer can detect features, e.g., cancerous growths, in any portion of the input image data, diffraction data, or a combination thereof.

RNNs, meanwhile, are neural networks with cyclical connections that can encode dependencies in time-series data, e.g., longitudinal study images of one or more subjects. An RNN may include an input layer that is configured to receive a sequence of time-series inputs, e.g., image data, diffraction pattern data, subject data, or any combination thereof collected over a period of time. An RNN may also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. Such an RNN can be used to determine time-series features or evolutions of features within the subject data.

One example of an RNN is a long short-term memory network (LSTM), which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate may be, for example, the logistic function.

Other examples of machine learning algorithms that can be used to process image data, diffraction pattern data, subject data, or any combination thereof are regression algorithms, decision trees, support vector machines, Bayesian networks, clustering algorithms, reinforcement learning algorithms, and the like.

The clustering algorithm may be, for example, a hierarchical clustering algorithm. A hierarchical clustering algorithm can be a clustering algorithm that clusters objects based on their proximity to other objects. For example, a hierarchical clustering algorithm can cluster image data, diffraction pattern data, subject data, or any combination thereof. The clustering algorithm can alternatively be a centroid-based clustering algorithm, e.g., a k-means clustering algorithm. A k-means clustering algorithm can partition n observations into k clusters, where each observation belongs to the cluster with the nearest mean. The mean can serve as a prototype for the cluster. In the context of image data, diffraction pattern data, subject data, or any combination thereof, a k-means clustering algorithm can generate distinct groups of data that are correlated with each other. Thereafter, each group of data can be associated with, e.g., a particular probability or diagnosis of cancer, based on knowledge about that subsystem, e.g., knowledge about previous diagnoses and data. The clustering algorithm can alternatively be a distribution-based clustering algorithm, e.g., a Gaussian mixture model or expectation maximization algorithm. Examples of other clustering algorithms are cosine similarity algorithms, topological data analysis algorithms, and hierarchical density-based clustering of applications with noise (HDB-SCAN).

The machine learning algorithm may be trained using a training dataset comprising image data, diffraction pattern data, subject data, or any combination thereof. The training dataset may be stored in the computer database for a specific pathology and/or physiological norm group. The training dataset may be obtained using the one or more diffraction apparatus. The training dataset may comprise micrograph images of stained tissue specimens. The training dataset may comprise information regarding a confirmation of a diagnosis for given set of data. For example, data comprising a plurality of images and diffraction patterns of a tissue suspected of being cancerous can also comprise a histological confirmation of the presence of the cancer in the tissue. In another example, a set of diffraction images can be accompanied by data regarding the longevity of the subject that the diffraction images were taken from. The computer database for the specific pathology and/or physiological norm group may be a remote computer database (e.g., a cloud-based database) or a local database (e.g., a computer system local to a diffraction apparatus). For example, the training dataset for breast cancer diagnostic indicators can be stored on a computer database with other breast cancer diagnostic data. The training dataset may be updated as new image data, diffraction pattern data, subject data, or any combination thereof is uploaded to the computer database. The updating may be an inclusion of the new data, a removal of the old data, or a combination thereof. For example, new image data can be added to the training dataset as it is taken to improve the quality of the training dataset. In another example, poor quality data may be removed from the training dataset when higher quality new data is added. The statistical analysis algorithm and/or machine learning algorithm (e.g., the data analytics algorithm) may be updated when the computer database or training dataset residing thereon is updated. For example, a machine learning algorithm can be retrained using the new training dataset to improve the efficacy of the machine learning algorithm in generating a computer-aided diagnostic indicator. The statistical analysis and/or machine learning algorithm may be continuously, periodically, or randomly updated and refined as the training dataset is updated. In this example, the revised statistical analysis and/or machine learning algorithm may be more accurate, specific, and/or sensitive in providing a probability or diagnosis than a previous version derived from a previous training dataset was.

Computer-aided diagnostic indicator: In some instances, the computer-aided diagnostic indicator for the individual subject may comprise an indicator of a likelihood that the individual subject has a cancer or other disease. The computer-aided diagnostic indicator for the individual subject may comprise an indicator of a likelihood that the individual subject has breast cancer. For example, a computer-aided diagnostic indicator can comprise a banded risk assessment for the individual subject (e.g., high risk, medium risk, low risk). The computer-aided diagnostic indicator may be displayed on a user interface of a device (e.g., a user interface on a computer screen, a user interface on a tablet). The computer-aided diagnostic indicator may be a report. The report may be a printed report. The report may comprise additional information. For example, the report may comprise a likelihood of the subject having a cancer, as well as the indicators that contributed to the generation of the report and a suggestion of possible next steps for the subject to take. The indicator may be a percentage (e.g., a percentage likelihood that the subject has the cancer), a risk band (e.g., high risk, medium risk, low risk), a comparison of factors (e.g., a list of factor indication a presence and a list of factors indicating an absence), or the like, or any combination thereof. The indicator of the likelihood that the individual subject has cancer may be an indicator of the likelihood that the individual subject has breast cancer.

In some instances, the computer-aided diagnostic indicator for the individual subject may comprise a diagnosis that the individual subject has a cancer or other disease. The computer-aided diagnostic indicator for the individual subject may comprise a diagnosis that the individual subject has breast cancer. The computer-aided diagnostic indicator may be generated at least in part using a statistical analysis algorithm and/or a machine learning algorithm. The computer-aided diagnostic indicator may be generated at least in part using input from a healthcare provider. For example, the healthcare provider can be presented with a list of indicators and risk bands, and the healthcare provider can make a final determination as to the diagnosis of the subject. In some instances, the computer-aided diagnostic indicator may have an accuracy, selectivity, and/or specificity of at least about 10%, 20%, 30%, 40%, 50%, 60%, 70%, 80%, 90%, 95%, 98%, 99%, 99.9%, or more. In some instances, the computer-aided diagnostic indicator may have an accuracy, selectivity, and/or specificity of at most about 99.9%, 99%, 98%, 95%, 90%, 80%, 70%, 60%, 50%, 40%, 30%, 20%, 10%, or less. Any of the lower and upper values described in this paragraph may be combined to form a range included within the present disclosure, for example, in some instances the computer-aided diagnostic indicator may have an accuracy, selectivity, and/or specificity that ranges from about 80% to about 99%. Those of skill in the art will recognize that, in some instances, the computer-aided diagnostic indicator may have an accuracy, selectivity, and/or specificity that has any value within this range, e.g., about 98.6%.

Figure 1B:
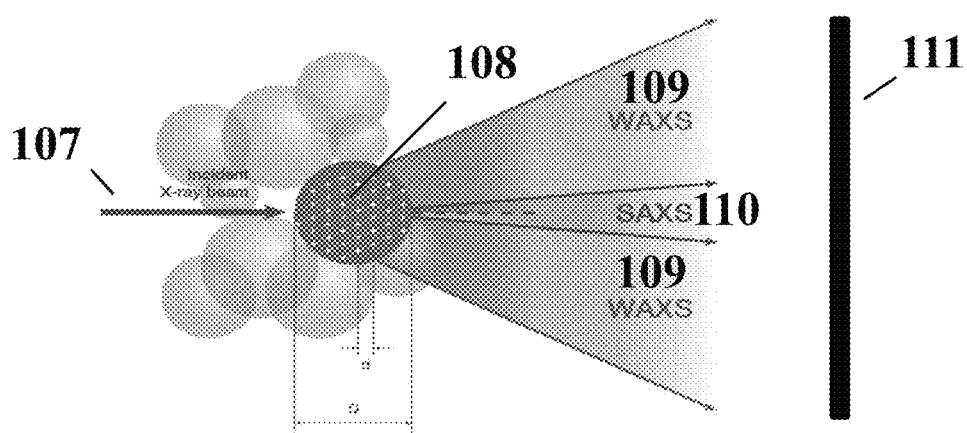
Figure 1C:
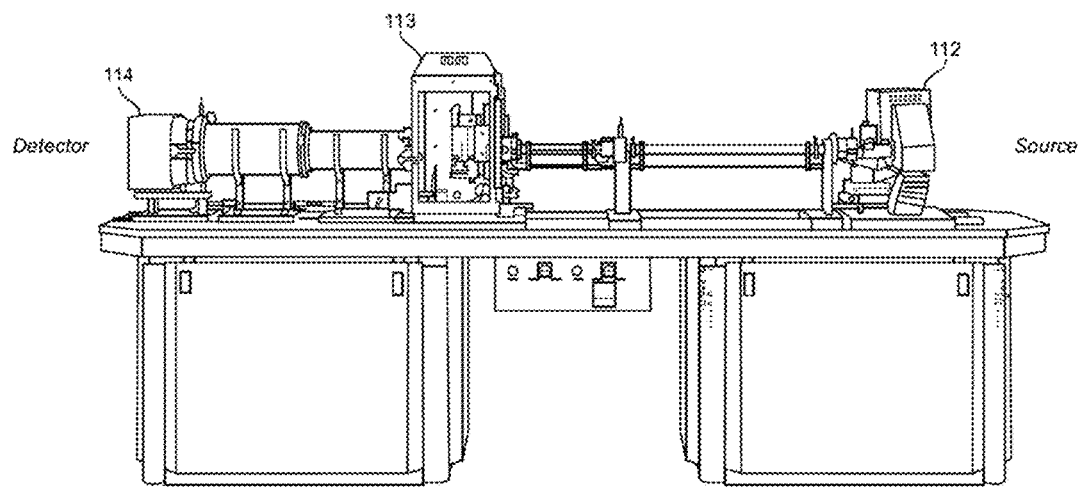

FIGS. 1A-1C show an overview of x-ray diffraction methodology. FIG. 1A is an overview of measuring a diffraction signal from a specimen 101. In some instances, the specimen may be a tissue (e.g., a breast tissue biopsy sample). The specimen may be a non-breast tissue specimen from the body of the subject. The specimen may be a tissue selected from the group consisting of spinal cord tissue, heart tissue, vascular tissue, lung tissue, liver tissue, kidney tissue, esophageal tissue, stomach tissue, intestinal tissue, pancreatic tissue, thyroid tissue, adrenal tissue, spleen tissue, lymphatic tissue, appendix tissue, breast tissue, bladder tissue, vaginal tissue, ovarian tissue, uterine tissue, penile tissue, testicular tissue, prostatic tissue, skeletal muscle tissue, skin, brain tissue, and non-brain tissue of the head and neck. The specimen may be of a thickness d. The thickness of the specimen may be such as to permit a transmission of the diffracted x-rays through the specimen to one or more detectors, such as detectors 102 and 103.

The detector, such as detectors 102 and 103 may be an x-ray detector. The detector may be a zero-dimensional (0D) detector (e.g., a photodiode). The detector may be a one-dimensional (1D) detector (e.g., a strip detector). The detector may be a two-dimensional (2D) detector (e.g., an array detector). The x-ray detector may be a film detector (e.g., a detector using silver halide crystals on a film), a phosphor plate detector (e.g., a plate of downshifting or down-converting phosphor that converts x-rays into light detectable by a photodetector), a semiconductor detector (e.g., a semiconductor charge coupled device (CCD), a complementary metal oxide semiconductor (CMOS) device), or the like, or any combination thereof. For example, a scintillator film can be applied over a CCD to detect x-rays. The diffraction apparatus may comprise one or more detectors. One detector of the plurality of detectors may be a reference detector 103. Another detector of the plurality of detectors may be a diffraction detector 102. In some cases, a single 2D detector is used in the same position as detector 103 to image the x-ray diffraction pattern. A single detector may be translated and/or rotated to detect the diffracted beam 105. For example, a 1D strip detector can be translated up and down in an arc to detect diffraction signal at different angles.

An x-ray diffraction image may be generated by directing an x-ray beam 104 towards the specimen 101. The x-ray beam may be a collimated x-ray beam. The interaction of the x-ray beam with the specimen may generate a diffracted beam 105 and an undiffracted beam 106. The undiffracted beam may be blocked with a beam block as not to saturate the one or more detectors. The angle 2Θ between the diffracted beam and the undiffracted beam may be related to a size of structuring of components of the specimen (e.g., related by the Bragg equation). The specimen 101 may be translated in they and/or z directions to generated diffraction patterns of different portions of the specimen. Alternatively, the x-ray beam 104 may be moved, rastered, deflected, or any combination thereof to generate diffraction patterns from different portions of the specimen.

FIG. 1B shows an overview of the different x-ray diffraction/scattering/refraction regimes. X-ray beam 107 may be directed into specimen 108, where the interaction between the x-ray beam and the specimen can generate x-ray signals 109 and 110. X-ray signals 109 may be present at wider angles and can thus be referred to as wide-angle x-ray scattering (WAXS) signals. The WAXS signals may be indicative of shorter-range ordering within the sample (e.g., atomic ordering on a scale of at most about ten nanometers). Alternatively, x-ray signals 110 may be present at smaller angles and can thus be referred to as small-angle x-ray scattering (SAXS) signals. The SAXS signals may be indicative of longer-range ordering within the sample (e.g., ordering on a scale of at least about ten nanometers). The x-ray signals 109 and 110 may propagate until reaching a detector 111. The detector may be a 2D detector that records the spatial intensity of the x-ray signals, thus generating an x-ray diffraction pattern. The distance between the specimen and the detector may impact the diffraction pattern data. For example, having the detector further from the specimen can improve the range of signals detected (e.g., higher 2Θ can be detected due to the larger diffraction cone) but reduce the resolution (e.g., a larger range of 2Θ is sampled by each pixel of the detector). Increasing a distance from the specimen may enable phase contrast imaging. The phase contrast imaging may result in increased edge enhancement and resolution.

FIG. 1C shows an example of a laboratory small angle x-ray diffraction instrument. The source 112 can generate an x-ray beam, such as x-ray beams 104 and 107. The x-ray beam may interact with the specimen in the interaction chamber 113, while the signals generated by the interaction can be detected by detector 114. The distance between the specimen and the detector, as well as the size of the detector, can influence the types of x-ray signals detected. For example, a larger detector positioned further from the specimen can record WAXS signals. The x-rays may travel through a vacuum environment to limit scattering and absorption by gasses. Alternatively, the x-rays may travel through a gas (e.g., the atmosphere) to make for a simpler instrument setup.

Figure 2A:
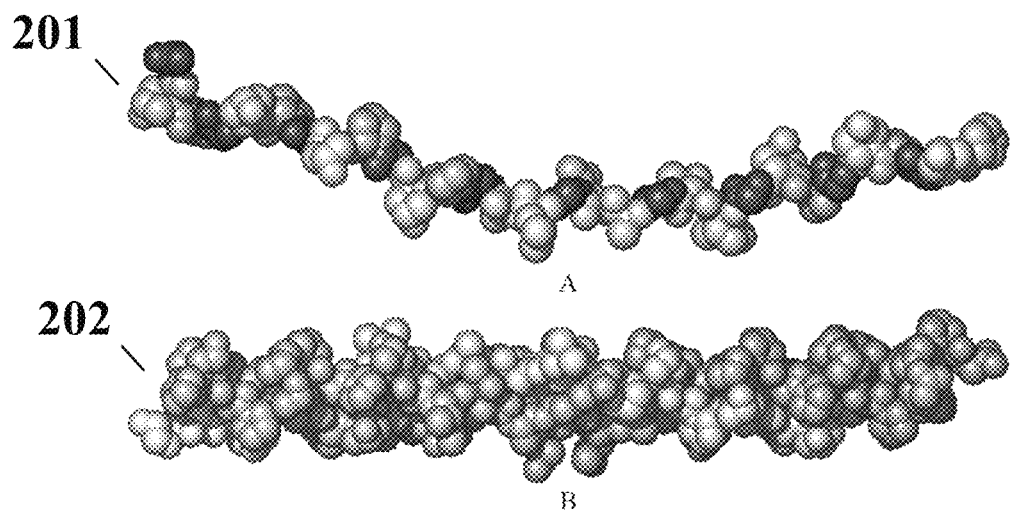
FIG. 2A shows an example of a disordered molecule and an ordered molecule.

FIG. 2A shows an example of a disordered molecule and an ordered molecule. The disordered molecule 201 may exhibit less efficient packing than the ordered molecule 202. As such, a diffraction pattern taken of a plurality of disordered molecules may have less prominent peaks due to the lack of ordered packing. For example, an x-ray diffraction image of solid sodium oleate can be broader than the corresponding x-ray diffraction image of sodium stearate due to the stearate having less disorder. The relationship between ordering and x-ray diffraction pattern intensity can be extended to larger biological systems (e.g., proteins, cell walls, fibers, muscles, etc.). For example, a well-ordered array of muscle fibers can have a stronger x-ray diffraction pattern than a disordered array. If a biological system shows a different ordering behavior when it is healthy versus anomalous, x-ray diffraction can provide information about the health of the tissue. For example, collagen tends to be well ordered in healthy tissues but disordered in unhealthy tissues. In this example, a SAXS measurement of a biopsy sample can determine the disorder state of the collagen and thus determine if the tissue is abnormal. Examples of deposits discernable by WAXS may include urea deposits (e.g., in gout), calcium deposits (e.g., calcium deposits in breast tissue), other organic crystals (e.g., proteins), other inorganic crystals (e.g., calcium fluoride), organic-inorganic crystalline hybrids (e.g., hemoglobin buildup), or the like, or any combination thereof. Examples of conditions discernable by SAXS may include cancers (e.g., carcinoma), plaque buildups, muscular diseases (e.g., atrophy), subcutaneous warts, or the like.

Figure 2B:
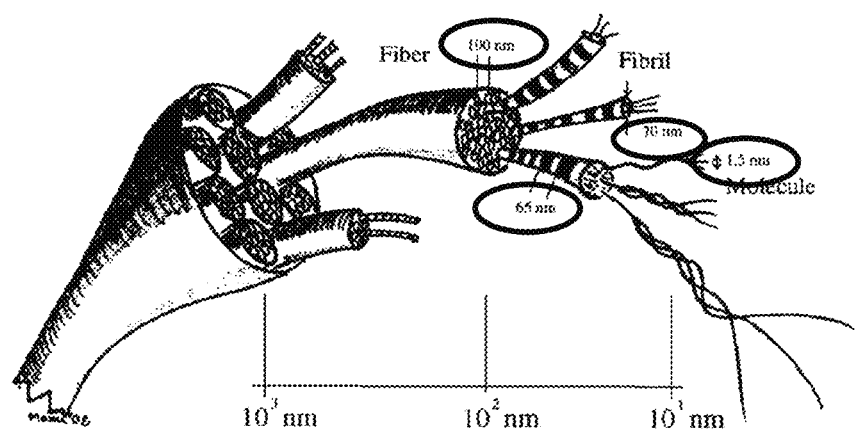
FIG. 2B shows an example of the relative scales of various biological objects (from "Small Angle X-Ray Scattering as a Diagnostic Tool for Breast Cancer", Sabeena Sidhu, BSc, MSc School of Physics, Monash University, Feb. 12, 2009).

FIG. 2B shows an example of the scales of various biological objects. The different scales may highlight the advantage of measuring SAXS, WAXS, micrograph images of stained tissue specimens, or any combination thereof at a same time. For example, a micrograph image can have a resolution of approximately 0.5 micrometers, which can make it impossible to view structural features having dimensions on the order of a few hundred nanometers or below. In this example, SAXS can provide details about the presence of ordering on the order of 10-10,000 nanometers and WAXS can provide details about the presence of ordering on the order of 0.1-10 nanometers. As shown in FIG. 2B, much of the fibrillar collagen in breast tissue may be of a scale of less than 100 nanometers, so information about the ordering of the collagen may be undetectable by conventional pathology lab imaging techniques but can be detected using x-ray scattering methods. Because tissue abnormalities can result in a change in the ordering of the tissue (e.g., cancer can disrupt collagen ordering), SAXS and/or WAXS can be a valuable addition to conventional pathology techniques.

FIGS. 3A-3B show examples of electron micrographs of collagen in normal tissue and in invasive carcinoma tissue. The healthy collagen 301 in FIG. 3A may present as a well-ordered tissue. The ordering of the fibrils, along with the homogenous nature of all of the tissue, can give rise to a strong diffraction pattern with peaks corresponding to the axial and meridional lengths of the collagen. The presence of these peaks can be an indicator of a healthy tissue. For example, a machine learning algorithm can be trained in part using healthy collagen tissues to associate the presence of diffraction peaks corresponding to the axial and meridional dimensions of the collagen with a healthy tissue. The invasive carcinoma tissue 302 of FIG. 3B may lack the long range ordering of the healthy tissue 301. As a result, a diffraction pattern taken of carcinoma tissue 302 may have weak or non-existent collagen peaks. This lack of peaks may be an indication of an invasive carcinoma. For example, a machine learning algorithm can use the lack of collagen peaks where there are expected to be collagen peaks as an indication of a presence of an invasive carcinoma.

Figure 4:
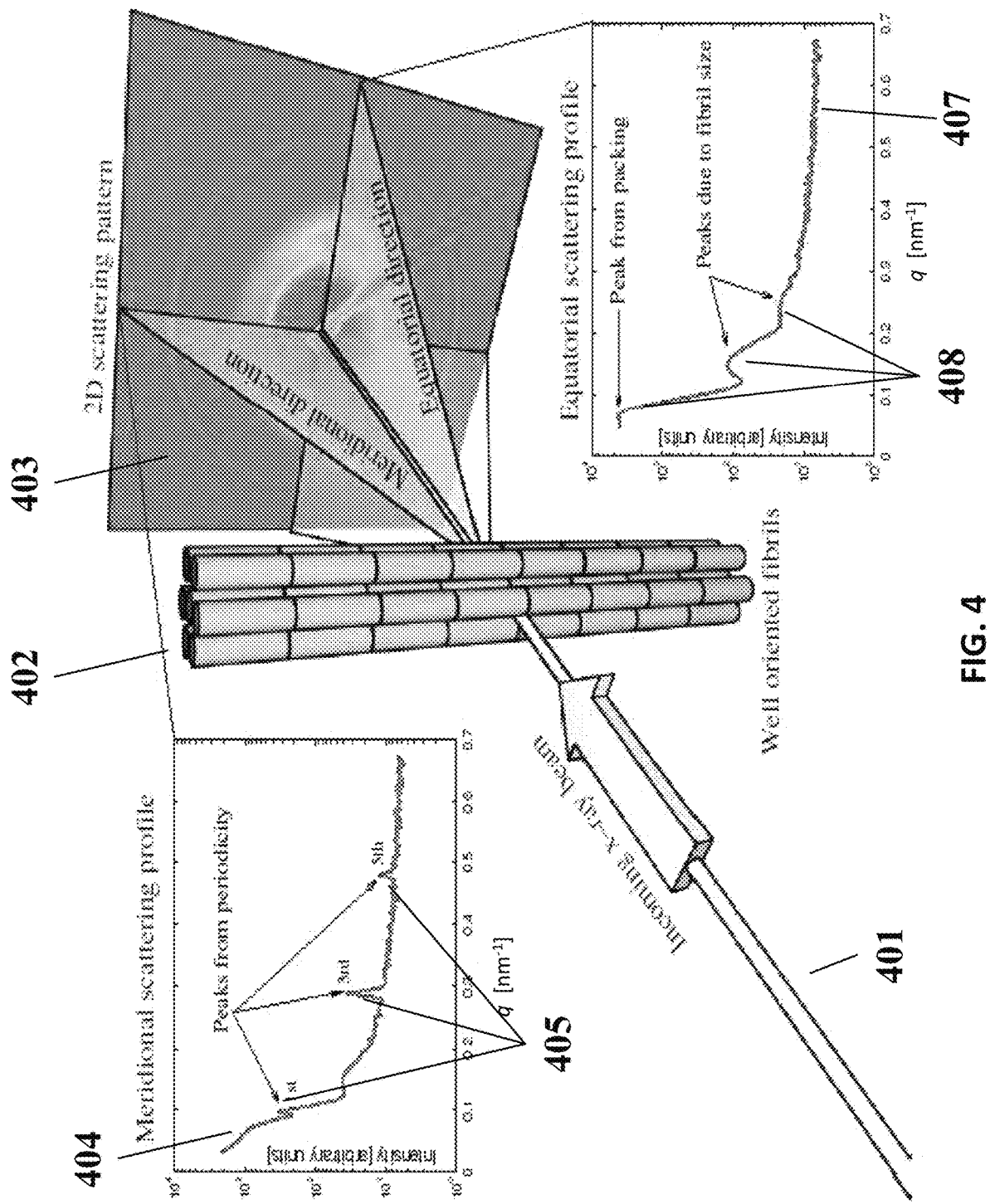
FIG. 4 shows examples of x-ray diffraction data generation.

FIG. 4 shows x-ray diffraction data generation. Incoming x-ray beam 401 can be directed towards fibril bundle 402. The periodicity of fibril bundle 402 can give rise to x-ray diffraction, which can be recorded as x-ray diffraction pattern 403. The intensity along the meridional axis of diffraction pattern 403 can be taken from the center of the pattern to the edge and can be plotted as meridional scattering profile 404. The meridional scattering profile can comprise peaks 405. The peaks can be the result of constructive interference in the x-ray diffraction giving rise to bands of higher intensity. In this example, the periodicity 406 of the fibrils can give rise to the diffraction peaks, with each peak representing a different nearest neighbor distance. The intensity along the equatorial direction of diffraction pattern 403 can be taken from the center of the diffraction pattern to the edge and plotted as equatorial scattering profile 407. The equatorial scattering profile may comprise peaks 408 that can be related to the packing of the fibrils as well as the size of the fibrils. In this example, since the fibrils are packed at a larger distance then the diameter 409 of the fibrils, the peak from the packing may be at a lower q value (e.g., larger distance) than the peaks from the fibril size.

The image data, diffraction pattern data, or a combination thereof may undergo statistical analysis. The statistical analysis may comprise determination of a pair-wise distance distribution function, determination of a Patterson function, a calculation of a Porod invariant, a cluster analysis, a dispersion analysis, determination of one or more molecular structural periodicities, or any combination thereof. The pair-wise distance distribution function may be derived from the x-ray diffraction data. The pair-wise distance distribution function may be a distribution of neighbors to a scatterer (e.g., an atom, a fibril, etc.). For example, a pair-wise distribution function of an atomic lattice can show the distribution of nearest neighbors to the atom as a function of distance. In another example, a pair wise distribution function of collagen fibrils can show the probability of finding another collagen fibril as a function of distance from the first fibril. The pair-wise distance distribution function may provide information regarding the local structure around the scatterer. The Patterson function may provide information related to the phase component of an x-ray diffraction based on the intensity of the diffraction pattern. The Patterson function may provide information regarding the electron density of the local environment of the specimen. The Porod invariant may be a model independent invariant that may be used to determine a volume fraction of the sample. The Porod invariant may depend on the volume of the scatterer, but not the form. For example, a sphere of volume 1 cubic micron and a cube of volume 1 cubic micron can have a same value of the Porod invariant. The cluster analysis may be a statistical analysis of the diffraction data. The cluster analysis may determine a presence of one or more clusters in the data. For example, diffraction data can be analyzed to determine clusters of data based on one or more components of the data. The dispersion analysis may determine a dispersion of different types of features within the sample. For example, a dispersion analysis of the size of scattering fibrils can generate a distribution of the different sizes of fibrils in the sample. The dispersion analysis may determine the dispersion shape, dispersion width, dispersion modality (e.g., bimodal), or the like, or any combination thereof. The determination of one or more molecular structural periodicities may be a determination of the crystal structure of a molecular array. For example, the structure of a urea crystal within a sample can be determined. In another example, the structural periodicity of tissue from a light spot identified in a mammogram can be determined from a biopsy of the breast tissue to identify the composition of the light spot. The determination of one or more molecular structural periodicities may provide an indicator of the identity of the molecule.

Figure 8:
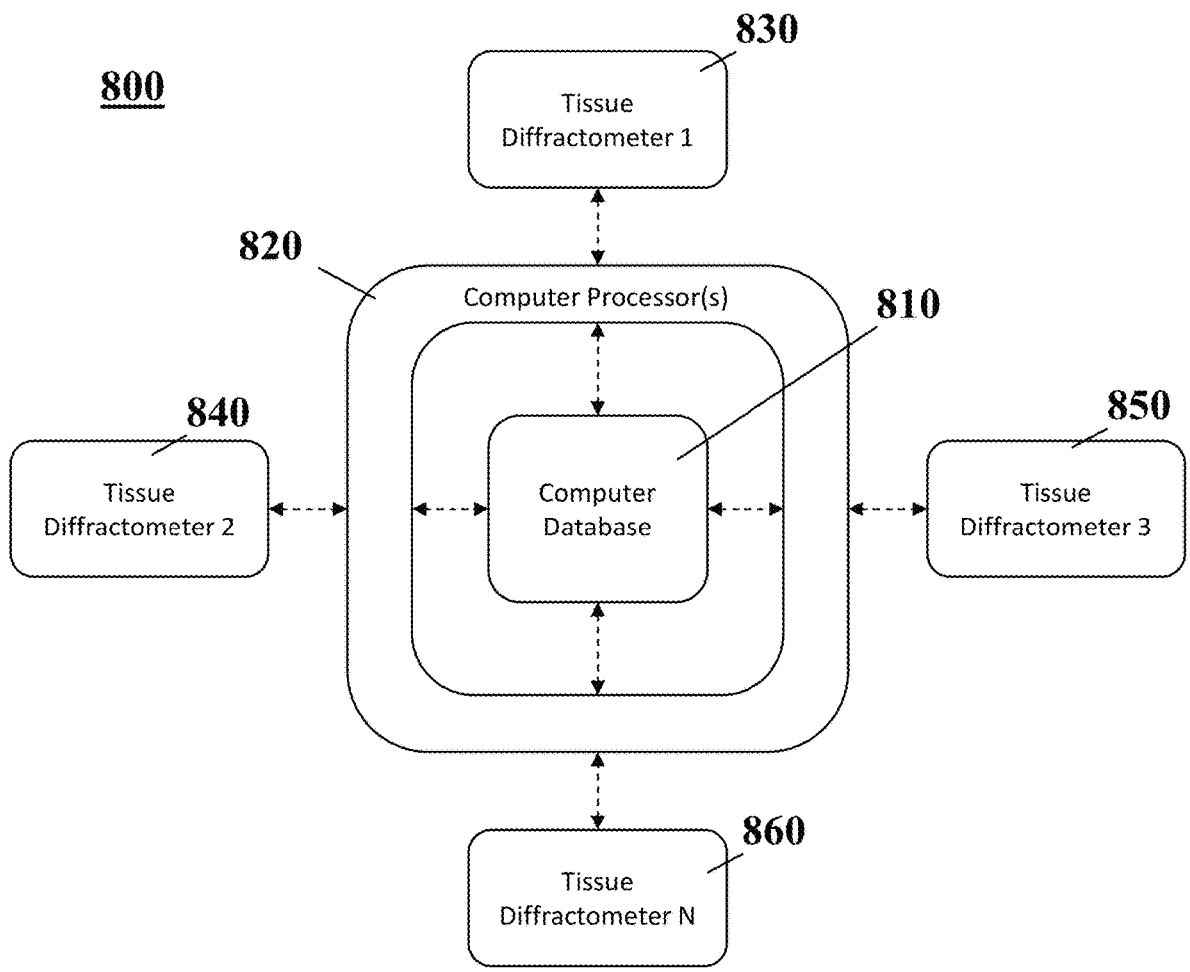
FIG. 8 shows a schematic of a plurality of diffraction apparatus operatively coupled to a computer database over a network.

FIG. 8 shows a schematic of a plurality of diffraction apparatus operatively coupled to a computer database over a network. The plurality of diffraction apparatus operatively coupled to the computer database over the network may be a global diagnostics system 800. The global in vitro diagnostics system may comprise a computer database 810. The computer database may be configured to store data (e.g., image data, diffraction pattern data, subject data, or any combination thereof). The central computer database may be encrypted. The computer database may be configured for compliance with health data privacy laws and regulations (e.g., HIPAA). The computer database may be a distributed computer database (e.g., a cloud-based database housed at a plurality of locations). The computer database may be configured to accept data from one or more diffraction apparatus 830, 840, 850, and/or 860 via one or more computer processors 820. The one or more computer processors may be configured to pre-process, process, and/or post-process the data as described elsewhere herein. The one or more computer processors may be coupled to the one or more diffraction apparatus via a network (e.g., a local network, the internet, a virtual private network). The one or more diffraction apparatus may be at least about 1, 5, 10, 25, 50, 75, 100, 250, 500, 750, 1,000, 2,500, 5,000, 10,000, 50,000, 100,000 or more diffraction apparatus. The one or more diffraction apparatus may be at most about 100,000, 50,000, 10,000, 5,000, 2,500, 1,000, 750, 500, 250, 100, 75, 50, 25, 10, 5, or less diffraction apparatus. The one or more diffraction apparatuses may be one or more of a same type of diffraction apparatus (e.g., a same model), or one or more of a different type of diffraction apparatus (e.g., one or more different models of diffraction apparatus). The computer processors 820 may be configured to periodically refine and update a statistical and/or machine learning based data analytics algorithm using data stored in the computer database 810. For example, the data analytics algorithm may be updated every month, every week, every day, or every hour. In some instances, the computer processors 820 and computer database 810 may be configured to continually refine a statistical and/or machine learning based data analytics algorithm. For example, each time new data is received from a diffraction apparatus, the computer processors 820 can access that new data from the computer database 810 to update the data analytics algorithm. The data analytics algorithm may be a data analytics algorithm and/or machine learning algorithm as described elsewhere herein.

Figure 9:
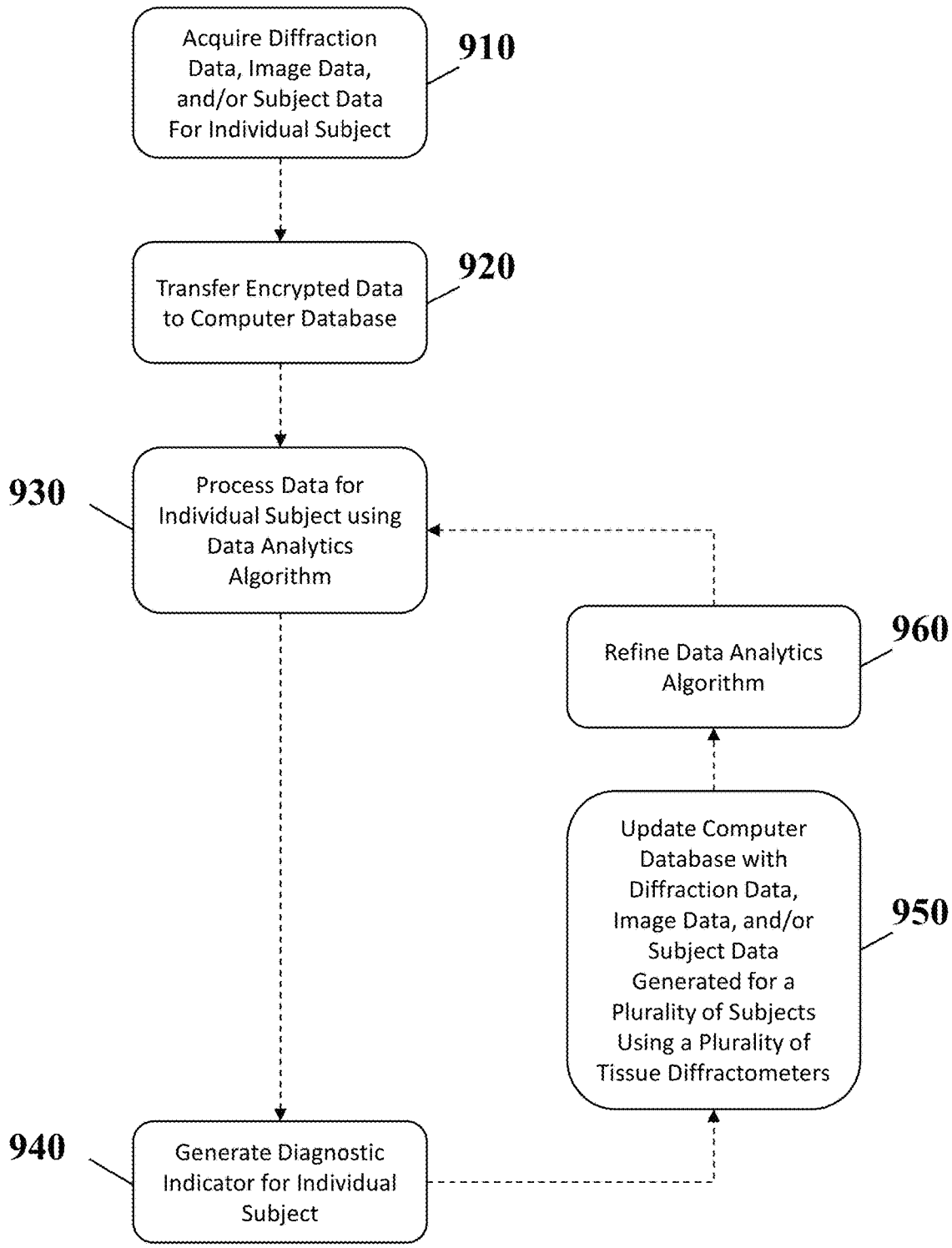
FIG. 9 shows an example schematic for a data collection and processing workflow.

FIG. 9 shows an example schematic for a data collection and processing workflow 900. In an operation 910, the process 900 may comprise acquiring diffraction data, image data, subject data, or any combination thereof for in vitro samples derived from an individual subject. The acquiring may be acquiring using a microscope, a diffraction-based instrument, or a combination of other tissue characterization instruments and diffraction apparatus.

In another operation 920, the process 900 may comprise transferring encrypted data to a computer database. The encrypted data may comprise image data, diffraction pattern data, subject data, or any combination thereof for one or more individual subjects. For example, the encrypted data can comprise all of the data taken from a radiology clinic in a day. In another example, the encrypted data can be data for in vitro samples from an individual subject served by a radiology clinic. The encrypted data may be encrypted using an asymmetric key encryption, a symmetric key encryption, or the like. The encrypted data may be encrypted by a computing device local to where the data was generated (e.g., a computer operatively coupled to a diffraction apparatus). The encrypted data may be stored locally before being transferred to the computer database. The encrypted data may be streamed (e.g., transferred in real-time or substantially real-time) to the computer database. The computer database may be a local computer database (e.g., a local computing cluster housed in the same facility as where the data was acquired) or a remote computer database (e.g., a cloud computing database). The encrypted data may be uncompressed data or uncompressed data.

In another operation 930, the process 900 may comprise processing data for the individual subject using a data analytics algorithm. The processing may be performed on one or more computer processors as described elsewhere herein. The processing may be encoded on a non-transitory computer readable medium. The data analytics algorithm may be a statistical analysis algorithm and/or a machine learning algorithm. The data analytics algorithm may be a convolutional neural network as described elsewhere herein. The data analytics algorithm may perform pre-processing, processing, and/or post-processing of diffraction data, image data, subject data, or any combination thereof. The pre-processing may comprise denoising (e.g., removing nose from the data), normalizing (e.g., standardizing data properties such as size, black level, maximum intensity, etc.), segmentation (e.g., dividing the data into sections comprising different features), masking (e.g., applying one or more masks to the data), enhancing edges and/or features, or the like, or any combination thereof. The processing may comprise determining a presence or absence of a feature in the data (e.g., determining a presence of a feature indicative of cancer), determining a severity of a feature in the data (e.g., determining the progression of a cancer), clustering data (e.g., clustering images based on the presence or absence of a feature), predicting a presence or absence of a feature in new data (e.g., using previously acquired images to generate a prediction of a presence of a feature in a new set of data), or the like, or any combination thereof. The post-processing may comprise formatting (e.g., formatting data for presentation to a subject or a healthcare worker), denoising, normalizing, masking, enhancing properties (e.g., contrast, edges), or the like, or any combination thereof.

In another operation 940, the process 900 may comprise generating a diagnostic indicator for the individual sample. The diagnostic indicator may be a computer-aided diagnostic indicator. The computer aided diagnostic indicator may be a computer readable report, a human readable report, or both. For example, the computer aided diagnostic indicator can be a report displayed on a user interface of a device. The diagnostic indicator may comprise information about a likelihood of a presence of a feature in the data (e.g., a presence of breast cancer), a severity of a presence of a feature (e.g., a prognosis based on the severity of the feature), one or more suggested treatments (e.g., a suggestion of a mastectomy for a severe breast cancer), additional information (e.g., locations of resources to help the subject understand the diagnostic indicator), subject data (e.g., the name of the subject the indicator is for), or the like, or any combination thereof. The diagnostic indicator may be generated on a same computer system as the data analytics algorithm was run on. The diagnostic indicator may be held until the healthcare provider provides an input. The input may be a payment (e.g., a payment from the subject, a payment from the subject's insurance), an agreement for the sample data for an individual subject to be used for training and/or validating future data analytics algorithms, or the like, or any combination thereof. For example, the subject can be informed that the diagnostic indicator is ready, and that the subject can sign a waiver allowing use of the subject's data.

In another operation 950, the process 900 may comprise updating the computer database with the, image data, diffraction data, subject data, or any combination thereof generated for a plurality of subjects using a plurality of diffraction apparatus. The updating may make additional data available to train a new data analytics algorithm or update an existing data analytics algorithm. The computer database may be updated with indicators of a confirmation of an indication made in a diagnostic indicator. For example, the database can be updated with information regarding the surgical confirmation of cancer in a patient for whom the diagnostic indicator indicated a likelihood of cancer. This updating may provide a confirmation of positive or negative results that can improve the accuracy of future diagnostic indicators. The data may be agglomerated for the plurality of subjects to generate a general classifier. For example, a database of stained tissue micrographs and diffraction patterns for breast biopsy samples can be used to generate a classifier for breast tissue. In another example, a database of brain tissue images and diffraction patterns can be used to generate a classifier for brain tissues.

In another operation 960, the process 900 may comprise refining the data analytics algorithm. The refining may comprise generating a new data analytics algorithm. The refining may comprise an updating of weights or other components within the data analytics algorithm. For example, the neural weights of a neural network can be updated based on the additional data for in vitro samples derived from the plurality of subjects. The refining of the data analytics algorithm may improve the sensitivity, specificity, accuracy, or any combination thereof of the data analytics algorithm. The refined data analytics algorithm may be used to process the data for tissue samples from another subject (e.g., used as the data analytics algorithm of operation 930).

Another application of the disclosed methods and systems is monitoring of therapeutic efficiency for cancer treatment or other diseases. Tissue samples collected from a patient after a period of receiving a therapeutic treatment are analyzed and evaluated for changes in sample data characteristics and clustering. As a result, the data analytics algorithm may, for example, plot patient sample data points in an n-dimensional space defined by two or more treatment parameters that describe the clustering of the sample data, and the distance or changes in distance between different clusters is calculated as a function of time. In some instances, for example, the proximity of a new data point to the previous data point(s), or the trajectory of certain data clusters (or the gradient of the trajectory) may be used as an indicator for the therapy's effectiveness and can be interpreted by physician in terms of therapeutic efficiency. Comparing the results of follow up assessments for multiple patients' samples may provide indications of the efficiency of certain drugs and treatments in particular groups of patients.

Figure 10:
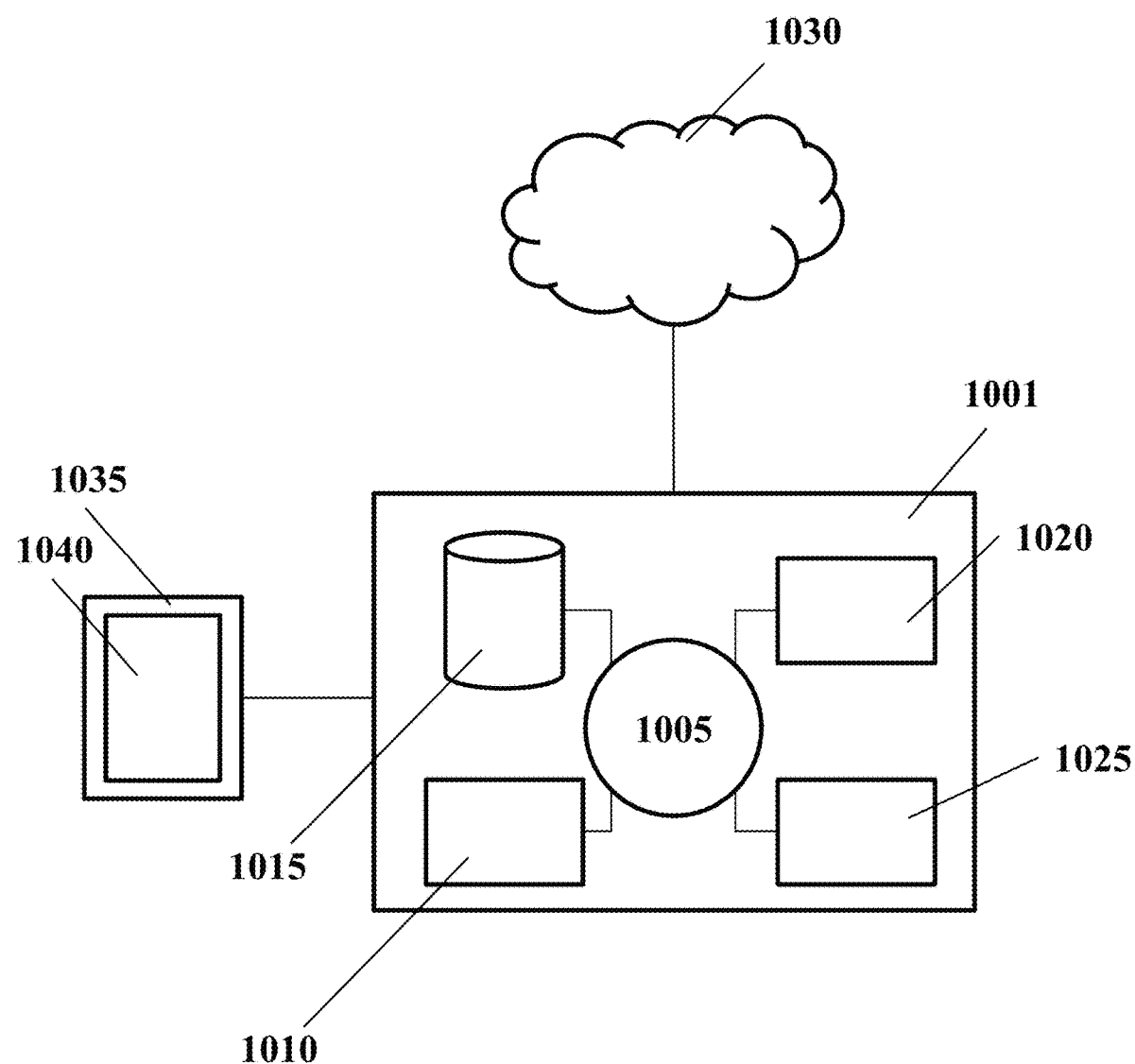
FIG. 10 shows a computer system that is programmed or otherwise configured to implement methods provided herein.

The present disclosure also provides computer systems that are programmed to implement methods of the disclosure. FIG. 10 shows a computer system 1001 that is programmed or otherwise configured to implement methods described elsewhere herein (e.g., obtaining data from one or more diffraction apparatus, processing the data, etc.). The computer system 1001 can regulate various aspects of the present disclosure, such as, for example, the processing of diffraction pattern data, subject data, or any combination thereof. The computer system 1001 can be an electronic device of a user or a computer system that is remotely located with respect to the electronic device. The electronic device can be a mobile electronic device. The computer system 1001 may be a post-classical computer system (e.g., a quantum computing system).

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1301 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., a cloud server). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine-readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, an interface for a healthcare or an individual subject to upload image data, diffraction pattern data, subject data, or any combination thereof to a computer database. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, be a machine learning algorithm as described elsewhere herein.

EXAMPLES

The following examples are illustrative of certain systems and methods described herein and are not intended to be limiting.

Example 1 X-Ray Diffraction Measurements of Breast Tissue

Figure 5A:
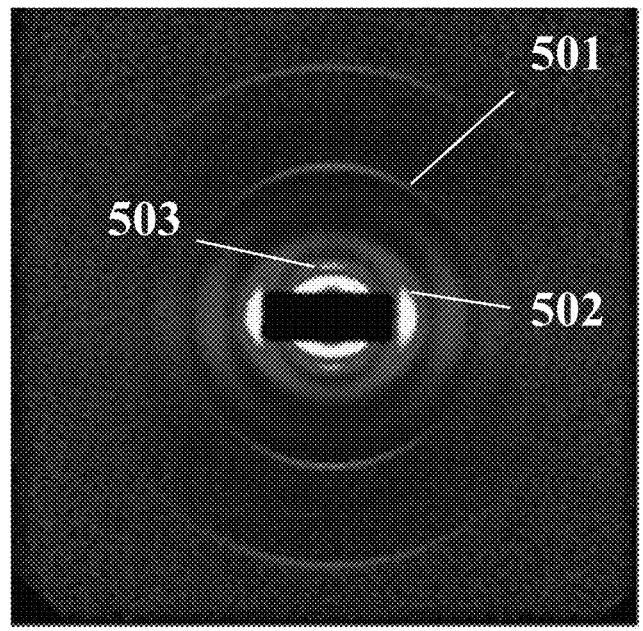
FIGS. 5A-5B show examples of small angle x-ray (SAXS) diffraction data.
Figure 5B:
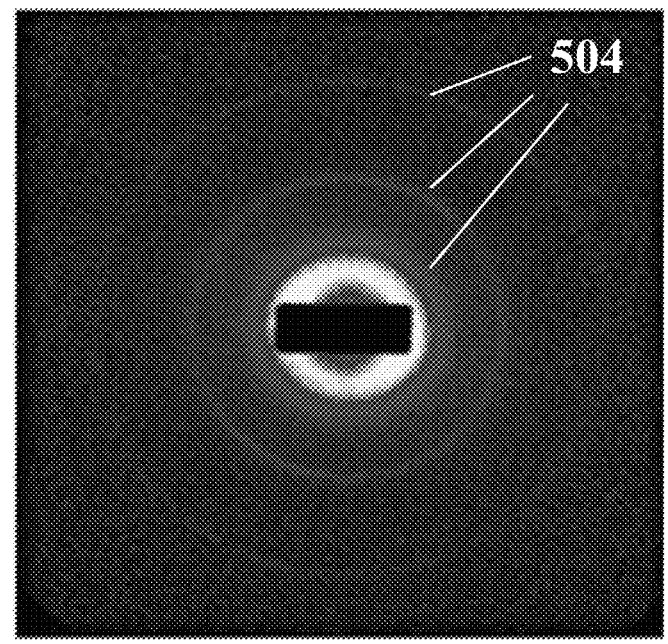

FIGS. 5A-5B show examples of small angle x-ray diffraction data. The normal tissue diffraction pattern of FIG.

5A exhibits clear peaks in the diffraction pattern, such as those called out as y-axis peak 501 and x-axis peak 502. The asymmetry of the size and distance of peaks 501 and 502 can be indicative of different size domains in each direction. Because the 2D diffraction pattern is in q space (e.g., with a dimension of 1/nm), the peak 501 can be indicative of shorter-range ordering as compared to peak 502 at lower q and thus larger range. The presence of diffraction spots 503 can be indicative of a presence of highly ordered and homogenous patterns (e.g., lines, lattices of points) within the tissue. Based on this diffraction pattern, the presence of asymmetric long- and short-range ordering can be an indicator of healthy breast tissue, such as a presence of uninterrupted collagen in the tissue or the presence of undisturbed fibrils. In contrast, the diffraction pattern of FIG. 5B, which was taken of breast tissue with a known disease, shows weak, symmetric diffraction peaks 504. As compared to the peaks in FIG. 5A, peaks 504 are weak and do not demonstrate asymmetric ordering. This is because the disease in the breast tissue results in a disruption of the tissue and a destruction of long-range order. For example, the tissues of FIGS. 3A-3B show the difference between healthy, ordered tissues and unhealthy, disordered tissues that can give rise to diffraction patterns as seen in FIGS. 5A-5B.

Figure 6A:
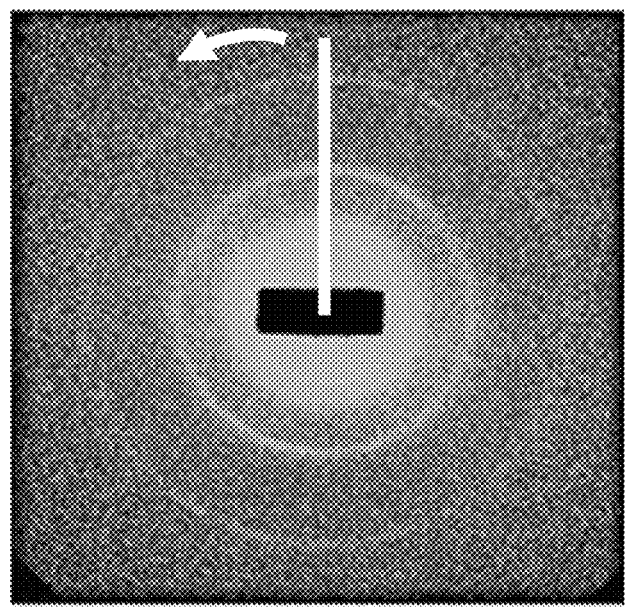
FIGS. 6A-6B show examples of small angle x-ray diffraction data from a breast tissue with a known disease.
Figure 6B:
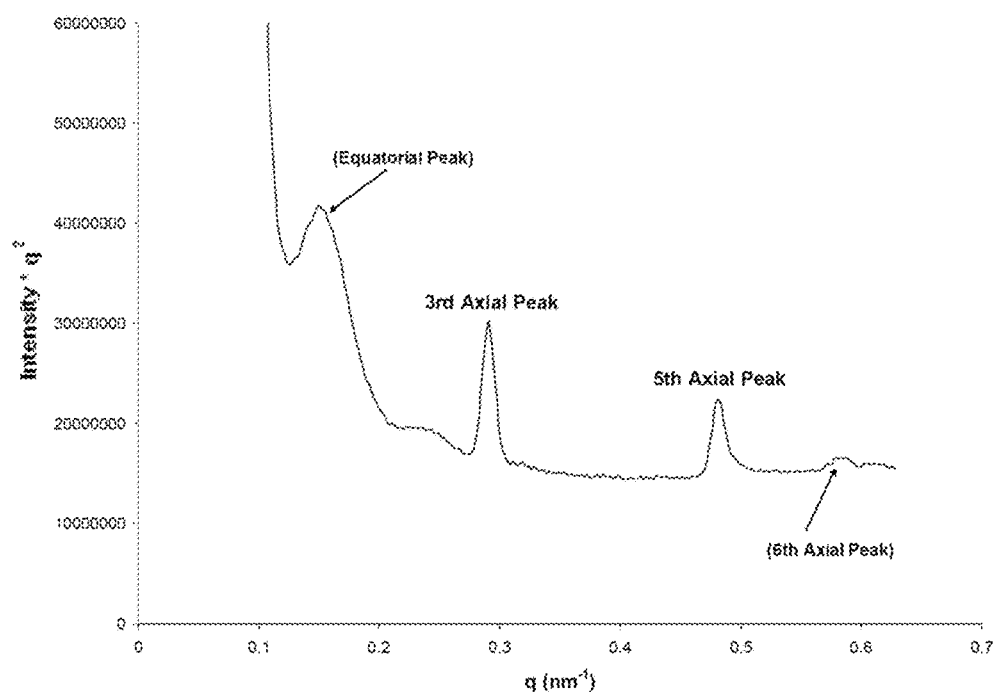

FIGS. 6A-6B show examples of small angle x-ray diffraction data from a breast tissue with a known disease. The diffraction pattern of FIG. 6A can be radially integrated (e.g., a slice of the image can be taken and rotated about the center as shown on the figure) to generate a 2D diffraction pattern as seen in FIG. 6B. Each of the high intensity regions of FIG. 6A can give rise to a peak in the diffraction pattern of FIG. 6B. While radially integrating can remove information about a distribution of the signals between axial and equatorial components, it can also improve signal to noise and provide a convenient way to display diffraction data. Additionally, knowing the approximate q value of the peak from the diffraction image can enable tracking of the peak in the diffraction pattern, as one can relate the q position from the image to a peak in the integrated pattern. The diffraction pattern of FIG. 6B is read where the center of the diffraction image corresponds to the far left of the pattern, and larger q corresponds to the edges of the diffraction image. Since q is in units of inverse space, the higher q peaks correspond to smaller spacings. For example, the fifth axial peak of FIG. 6B corresponds to an ordering with a feature size of approximately 0.5 inverse nanometers. The intensities of the peaks, as well as the position, width (e.g., full width at half maximum), shape (e.g., gaussian shape, Lorentzian shape), or any combination thereof can be indicators of the order state of the tissue, which can be related to a presence or absence of a disease. Diffraction images such as that of FIG. 6A, as well as diffraction patterns such as that of FIG. 6B can be used as input data for a machine learning algorithm configured to detect a presence or absence of a cancer.

Figure 7:
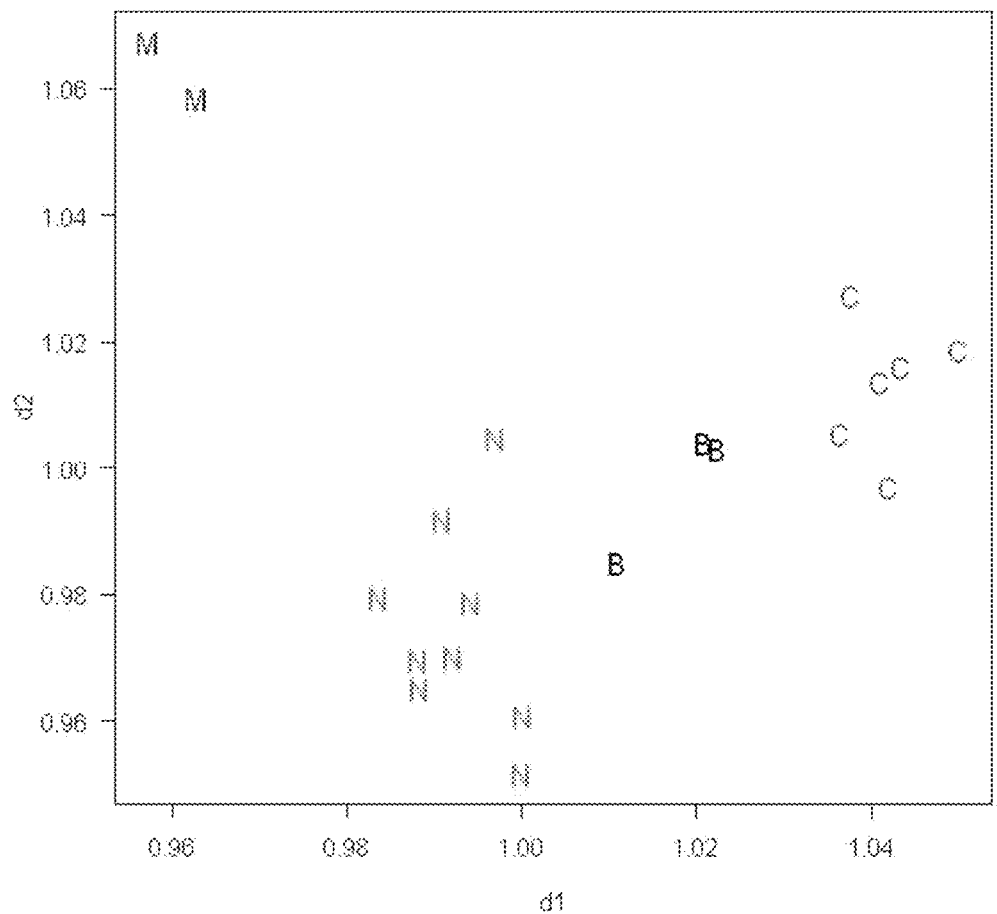
FIG. 7 shows an example of data extracted from x-ray diffraction patterns that has been plotted to illustrate the clustering for different tissue types (from: "Small Angle X-Ray Scattering as a Diagnostic Tool for Breast Cancer", Sabeena Sidhu, BSc, MSc School of Physics, Monash University, Feb. 12, 2009).

FIG. 7 shows an example of data extracted from x-ray diffraction patterns that has been plotted to illustrate the clustering for different tissue types. In this example, the intensity of two peaks, d1 and d2, in a plurality of datasets were plotted against each other to form the scatter plot. A convolutional neural network can then process the data to cluster the points based not only on the relative intensities of the two peaks, but also based on other data from the diffraction patterns and related image data. The neural network can then assign indicators to each of the clusters to aid in a diagnosis. In this example, the clusters were labeled as non-cancerous (N), malignant (M), suspicious (B), and indicative of calcium deposits (C). In an example, a new diffraction pattern is processed and shows a d1 peak intensity of 0.91 and a d2 peak intensity of 1.05. In this example, the new diffraction pattern can be classified as being of a malignant breast sample, as the new data fits best with the malignant cluster. The neural network can then be updated with the new data to improve the effectiveness of the neural network for future data.

Further Aspects of the Disclosure

1. A system comprising: (a) one or more diffraction apparatuses operatively coupled to a computer database over a network, wherein the one or more diffraction apparatuses are configured to collect sample data comprising diffraction pattern data for in vitro samples and transfer the sample data, or data derived therefrom, to the computer database over the network; and (b) one or more computer processors operatively coupled to the one or more diffraction apparatuses, wherein the one or more computer processors are individually or collectively configured to: (i) receive the sample data, or the data derived therefrom, from at least one of the one or more diffraction apparatuses; (ii) transmit the sample data, or the data derived therefrom, from at least one of the one or more diffraction apparatuses to the computer database; and (iii) process the sample data, or the data derived therefrom, for an individual in vitro sample using a data analytics algorithm that provides a computer-aided diagnostic indicator for the in vitro sample or for a subject from which the in vitro sample was derived.

2. The system of aspect 1, further comprising a user interface that allows an individual subject or a healthcare provider to upload the individual subject's sample data for an in vitro sample to the computer database in exchange for processing of the sample data to receive the computer-aided diagnostic indicator for the in vitro sample or for the individual subject.

3. The system of aspect 2, wherein the user interface is further configured to allow an individual subject or their healthcare provider to make payments or upload an individual subject's signed consent form.

4. The system of any one of aspects 1 to 3, comprising two or more diffraction apparatuses located in two or more different geographic locations.

5. The system of any one of aspects 1 to 4, wherein the one or more diffraction apparatuses comprise a data encryption device that includes a global positioning system (GPS) positioning sensor and generates encrypted sample data, and wherein when transferred to the computer database the encrypted sample data is used to track changes in location of the one or more diffraction apparatuses.

6. The system of any one of aspects 1 to 5, wherein the one or more diffraction apparatuses are configured to perform small angle X-ray scattering (SAXS) measurements.

7. The system of any one of aspects 1 to 6, wherein the one or more diffraction apparatuses are configured to perform wide angle X-ray scattering (WAXS) measurements.

8. The system of any one of aspects 1 to 7, wherein the in vitro samples comprise a surgical sample, a resection sample, a pathology sample, a biopsy sample, or any combination thereof.

9. The system of any one of aspects 1 to 8, wherein the sample data further comprises pathology lab image data, subject data, or any combination thereof.

10. The system of any one of aspects 1 to 9, wherein the computer database resides on a central server.

11. The system of any one of aspects 1 to 10, wherein the computer database resides in the cloud.

12. The system of aspect 10 or aspect 11, wherein the sample data transferred to the computer database are depersonalized prior to the transfer.

13. The system of aspect 12, wherein a key for mapping the depersonalized sample data stored in the computer database to an individual subject is stored in a local institutional database or in the individual subject's personal files.

14. The system of any one of aspects 1 to 13, wherein the data analytics algorithm comprises a statistical analysis of diffraction pattern data or a function thereof.

15. The system of aspect 14, wherein the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

16. The system of aspect 15, wherein the statistical analysis comprises a determination of a structural periodicity of collagen.

17. The system of aspect 15, wherein the statistical analysis comprises a determination of a structural periodicity of one or more lipids.

18. The system of aspect 15, wherein the statistical analysis comprises a determination of a structural periodicity of a tissue.

19. The system of any one of aspects 1 to 18, wherein the data analytics algorithm comprises a machine learning algorithm.

20. The system of aspect 19, wherein the machine learning algorithm comprises a supervised learning algorithm, an unsupervised learning algorithm, a semi-supervised learning algorithm, a reinforcement learning algorithm, a deep learning algorithm, or any combination thereof.

21. The system of aspect 20, wherein the machine learning algorithm is a deep learning algorithm.

22. The system of aspect 21, wherein the deep learning algorithm is a convolutional neural network, a recurrent neural network, or a recurrent convolutional neural network.

23. The system of any one of aspects 19 to 22, wherein the machine learning algorithm is trained using a training dataset comprising pathology lab image data, diffraction pattern data, subject data, or any combination thereof from one or more control samples.

24. The system of aspect 23, wherein the training dataset is updated as new sample data are uploaded to the computer database.

25. The system of any one of aspects 1 to 24, wherein the sample data further comprises subject data comprising an individual subject's age, sex, ancestry data, genetic data, behavioral data, or any combination thereof, wherein the sample is from the individual subject.

26. The system of any one of aspects 1 to 25, wherein the computer-aided diagnostic indicator for the in vitro sample comprises an indicator of a likelihood that the sample is positive or negative for a cancer.

27. The system of aspect 26, wherein the cancer comprises breast cancer, brain cancer, bone cancer, lung cancer, cervical cancer, bladder cancer, head and neck cancer, kidney cancer, intestinal cancer, liver cancer, ovarian cancer, pancreatic cancer, prostate cancer, skin cancer, throat cancer, oral cancer, vaginal cancer, or any combination thereof.

28. The system of any one of aspects 9 to 27, wherein the pathology lab image data comprises micrographs of stained in vitro tissue specimens.

29. The system of any one of aspects 1 to 28, wherein the system is used to monitor the efficacy of a cancer therapeutic treatment.

30. A method comprising: a) using one or more diffraction apparatuses to acquire sample data comprising diffraction pattern data for in vitro samples, wherein the one or more diffraction apparatuses are operatively coupled to a computer database over a network and are configured to transfer the sample data, or data derived therefrom to the computer database over the network; b) using one or more computer processors operatively coupled to the one or more diffraction apparatuses to: i. receive the sample data, or the data derived therefrom, from at least one of the one or more diffraction apparatuses; ii. transmit the sample data, or the data derived therefrom, from at least one of the one or more diffraction apparatuses to the computer database; and iii. process the sample data, or the data derived therefrom, for an individual in vitro sample using a data analytics algorithm that provides a computer-aided diagnostic indicator for the in vitro sample or for a subject from which the in vitro sample was derived.

31. The method of aspect 30, further comprising providing a user interface that allows an individual subject or a healthcare provider to upload the individual subject's sample data to the computer database in exchange for processing of the sample data to receive the computer-aided diagnostic indicator for the in vitro sample or for the individual subject.

32. The method of aspect 31, wherein the user interface is further configured to allow the individual subject or the healthcare provider to make payments or upload a signed consent form for use of the sample data.

33. The method of any one of aspects 30 to 32, wherein the one or more diffraction apparatuses comprise a plurality of diffraction apparatuses located in different geographic locations.

34. The method of any one of aspects 30 to 33, wherein the one or more diffraction apparatuses comprise a data encryption device that includes a global positioning system (GPS) positioning sensor and generates encrypted data, and wherein when transferred to the computer database the encrypted data is used to track changes in locations of the one or more diffraction apparatuses.

35. The method of any one of aspects 30 to 34, wherein the one or more diffraction apparatuses are configured to perform small angle X-ray scattering (SAXS) measurements.

36. The method of any one of aspects 30 to 35, wherein the one or more diffraction apparatuses are configured to perform wide angle X-ray scattering (WAXS) measurements.

37. The method of any one of aspects 30 to 36, wherein the sample data further comprises pathology lab image data, subject data, or any combination thereof.

38. The method of any one of aspects 30 to 37, wherein the computer database resides on a central server.

39. The method of any one of aspects 30 to 38, wherein the computer database resides in the cloud.

40. The method of any one of aspects 30 to 39, wherein the sample data are depersonalized prior to the transfer.

41. The method of aspect 40, wherein a key for mapping the depersonalized sample data stored in the computer database to an individual subject is stored in a local institutional database or in the individual subject's personal files.

42. The method of any one of aspects 30 to 41, wherein the data analytics algorithm comprises a statistical analysis of diffraction pattern data or a function thereof.

43. The method of aspect 42, wherein the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

44. The method of aspect 43, wherein the statistical analysis comprises a determination of a structural periodicity of collagen.

45. The method of aspect 43, wherein the statistical analysis comprises a determination of a structural periodicity of a lipid.

46. The method of aspect 43, wherein the statistical analysis comprises a determination of a structural periodicity of a tissue.

47. The method of any one of aspects 30 to 46, wherein the data analytics algorithm comprises a machine learning algorithm.

48. The method of aspect 47, wherein the machine learning algorithm comprises a supervised learning algorithm, an unsupervised learning algorithm, a semi-supervised learning algorithm, a reinforcement learning algorithm, a deep learning algorithm, or any combination thereof.

49. The method of aspect 48, wherein the machine learning algorithm is a deep learning algorithm.

50. The method of aspect 49, wherein the deep learning algorithm is a convolutional neural network, a recurrent neural network, or a recurrent convolutional neural network.

51. The method of any one of aspects 47 to 50, wherein the machine learning algorithm is trained using a training dataset comprising pathology lab image data, diffraction pattern data, subject data, or any combination thereof from one or more control samples.

52. The method of aspect 51, wherein the training dataset is updated as new sample data are uploaded to the computer database.

53. The method of any one of aspects 30 to 52, wherein the sample data further comprises subject data comprising an individual subject's age, sex, ancestry data, genetic data, behavioral data, or any combination thereof.

54. The method of any one of aspects 30 to 53, wherein the computer-aided diagnostic indicator for the in vitro sample comprises an indicator of the likelihood that the sample is positive or negative for a cancer.

55. The method of aspect 54, wherein the cancer comprises breast cancer, brain cancer, bone cancer, lung cancer, cervical cancer, bladder cancer, head and neck cancer, kidney cancer, intestinal cancer, liver cancer, ovarian cancer, pancreatic cancer, prostate cancer, skin cancer, throat cancer, oral cancer, vaginal cancer, or any combination thereof.

56. The method of any one of aspects 37 to 55, wherein the pathology lab image data comprises micrographs of stained in vitro tissue specimens.

57. The method of any one of aspects 30-56, further comprising collecting different in vitro samples from an individual subject at different time points, and repeating a)-b) at the different time points to monitor a change over time of a condition, disease, or disorder associated with the individual subject upon a determination of the individual sample as being positive for the condition, disease, or disorder.

58. The method of aspect 57, wherein the different time points are within a time period during which the individual subject is subjected to a treatment or a therapeutic intervention.

59. The method of aspect 57, further comprising determining an efficacy of the treatment or the therapeutic intervention.

60. The method of any one of aspects 30 to 59, wherein the in vitro samples comprise a tissue sample.

61. The method of any one of aspects 30 to 60, wherein the in vitro samples comprise a surgical sample, a resection sample, a pathology sample, a biopsy sample, or any combination thereof.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system comprising:
   (a) one or more diffraction apparatuses operatively coupled to a computer database over a network, wherein the one or more diffraction apparatuses are configured to collect sample data comprising diffraction pattern data for in vitro samples and transfer the sample data, or data derived therefrom, to the computer database over the network; and
   (b) one or more computer processors operatively coupled to the one or more diffraction apparatuses, wherein the one or more computer processors are individually or collectively configured to:
      (i) receive the sample data, or the data derived therefrom, from at least one of the one or more diffraction apparatuses;
      (ii) transmit the sample data, or the data derived therefrom, from at least one of the one or more diffraction apparatuses to the computer database; and
      (iii) process the sample data, or the data derived therefrom, for an individual in vitro sample using a data analytics algorithm that provides a computer-aided diagnostic indicator for the in vitro sample or for a subject from which the in vitro sample was derived, wherein the data analytics algorithm comprises a statistical analysis of diffraction pattern data or a function thereof.

2. The system of claim 1, further comprising a user interface that allows an individual subject or a healthcare provider to upload the individual subject's sample data for an in vitro sample to the computer database in exchange for processing of the sample data to receive the computer-aided diagnostic indicator for the in vitro sample or for the individual subject.

3. The system of claim 1, comprising two or more diffraction apparatuses located in two or more different geographic locations.

4. The system of claim 1, wherein the one or more diffraction apparatuses comprise a data encryption device that includes a global positioning system (GPS) positioning sensor and generates encrypted sample data, and wherein when transferred to the computer database the encrypted sample data is used to track changes in location of the one or more diffraction apparatuses.

5. The system of claim 1, wherein the one or more diffraction apparatuses are configured to perform small angle X-ray scattering (SAXS) measurements or wide angle X-ray scattering (WAXS) measurements.

6. The system of claim 1, wherein the in vitro samples comprise a surgical sample, a resection sample, a pathology sample, a biopsy sample, or any combination thereof.

7. The system of claim 1, wherein the sample data further comprises pathology lab image data, subject data, or any combination thereof.

8. The system of claim 7, wherein the sample data comprises pathology lab image data, and wherein the pathology lab image data comprises micrographs of stained in vitro tissue specimens.

9. The system of claim 1, wherein the sample data transferred to the computer database are depersonalized prior to the transfer.

10. The system of claim 9, wherein a key for mapping the depersonalized sample data stored in the computer database to an individual subject is stored in a local institutional database or in the individual subject's personal files.

11. The system of claim 1, wherein the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

12. The system of claim 11, wherein the statistical analysis comprises a determination of a structural periodicity of collagen, a structural periodicity of one or more lipids, or a structural periodicity of a tissue.

13. The system of claim 1, wherein the data analytics algorithm comprises a machine learning algorithm, wherein the machine learning algorithm comprises a supervised learning algorithm, an unsupervised learning algorithm, a semi-supervised learning algorithm, a reinforcement learning algorithm, a deep learning algorithm, or any combination thereof.

14. The system of claim 13, wherein the machine learning algorithm is a deep learning algorithm, and wherein the deep learning algorithm is a convolutional neural network, a recurrent neural network, or a recurrent convolutional neural network.

15. The system of claim 13, wherein the machine learning algorithm is trained using a training dataset comprising pathology lab image data, diffraction pattern data, subject data, or any combination thereof from one or more control samples.

16. The system of claim 15, wherein the training dataset is updated as new sample data are uploaded to the computer database.

17. The system of claim 1, wherein the sample data further comprises subject data comprising an individual subject's age, sex, ancestry data, genetic data, behavioral data, or any combination thereof, wherein the sample is from the individual subject.

18. The system of claim 1, wherein the computer-aided diagnostic indicator for the in vitro sample comprises an indicator of a likelihood that the sample is positive or negative for a cancer.

19. The system of claim 18, wherein the cancer comprises breast cancer, brain cancer, bone cancer, lung cancer, cervical cancer, bladder cancer, head and neck cancer, kidney cancer, intestinal cancer, liver cancer, ovarian cancer, pancreatic cancer, prostate cancer, skin cancer, throat cancer, oral cancer, vaginal cancer, or any combination thereof.

20. The system of claim 1, wherein the system is used to monitor the efficacy of a cancer therapeutic treatment.

* * * * *